US008557974B2

United States Patent
Paitan

(10) Patent No.: US 8,557,974 B2
(45) Date of Patent: *Oct. 15, 2013

(54) METHODS, COMPOSITIONS AND KITS FOR DETECTION AND ANALYSIS OF ANTIBIOTIC-RESISTANT BACTERIA

(75) Inventor: Yosef Paitan, Kfar Saba (IL)

(73) Assignee: Molecular Detection Inc., Wayne, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/466,997

(22) Filed: May 8, 2012

(65) Prior Publication Data

US 2012/0225429 A1 Sep. 6, 2012

Related U.S. Application Data

(63) Continuation of application No. 13/229,598, filed on Sep. 9, 2011, which is a continuation of application No. 13/205,496, filed on Aug. 8, 2011, which is a continuation of application No. 13/178,807, filed on Jul. 8, 2011, now Pat. No. 8,362,228, which is a continuation of application No. 13/038,035, filed on Mar. 1, 2011, which is a continuation of application No. 12/106,137, filed on Apr. 18, 2008, now Pat. No. 8,017,337.

(60) Provisional application No. 60/907,848, filed on Apr. 19, 2007.

(51) Int. Cl.
*C07H 21/04* (2006.01)
*C12Q 1/68* (2006.01)

(52) U.S. Cl.
USPC ............... 536/24.33; 435/6.12; 536/24.32

(58) Field of Classification Search
None
See application file for complete search history.

(56) References Cited

U.S. PATENT DOCUMENTS

| | | | |
|---|---|---|---|
| 4,237,051 A | 12/1980 | McCombie | |
| 4,282,236 A | 8/1981 | Broom | |
| 4,743,679 A | 5/1988 | Cohen et al. | |
| 5,004,686 A | 4/1991 | Cohen et al. | |
| 5,032,510 A | 7/1991 | Kovacevic et al. | |
| 5,158,878 A | 10/1992 | Prinz et al. | |
| 5,210,015 A | 5/1993 | Gelfand et al. | |
| 5,292,874 A | 3/1994 | Milliman | |
| 5,389,521 A | 2/1995 | Krivan et al. | |

(Continued)

FOREIGN PATENT DOCUMENTS

| | | |
|---|---|---|
| CA | 2348042 | 6/2001 |
| EP | 0887 424 A2 | 12/1998 |
| EP | 1529847 A1 | 5/2005 |
| WO | WO 2007023461 A2 | 3/2007 |

OTHER PUBLICATIONS

Brakstad, et al., "Detection of *Staphylococcus aureus* by Polymerase Chain Reaction Amplification of the nuc Gene", J. Clin Microbiology, 1992, vol. 30, No. 7; pp. 1654-1660.

(Continued)

*Primary Examiner* — Samuel Woolwine
(74) *Attorney, Agent, or Firm* — Morgan, Lewis & Bockius LLP

(57) ABSTRACT

The present invention relates generally to detection of antibiotic-resistant bacteria in a sample. In particular, the invention provides methods, compositions and kits for detecting and analyzing methicillin-resistant *Staphylococcus aureus* (MRSA) and other methicillin-resistant bacteria in a sample.

3 Claims, 4 Drawing Sheets

(56) References Cited

U.S. PATENT DOCUMENTS

| | | | |
|---|---|---|---|
| 5,437,975 | A | 8/1995 | McClelland et al. |
| 5,437,978 | A | 8/1995 | Ubukata et al. |
| 5,447,914 | A | 9/1995 | Travis et al. |
| 5,468,852 | A | 11/1995 | Ohashi et al. |
| 5,487,985 | A | 1/1996 | McClelland et al. |
| 5,516,898 | A | 5/1996 | Ohashi et al. |
| 5,525,718 | A | 6/1996 | Ohashi et al. |
| 5,582,974 | A | 12/1996 | Nietuspki et al. |
| 5,582,975 | A | 12/1996 | Milliman |
| 5,587,307 | A | 12/1996 | Alborn, Jr. et al. |
| 5,646,014 | A | 7/1997 | Hara |
| 5,648,240 | A | 7/1997 | Hook et al. |
| 5,700,928 | A | 12/1997 | Hodgson et al. |
| 5,702,895 | A | 12/1997 | Matsunaga et al. |
| 5,770,375 | A | 6/1998 | Ohno et al. |
| 5,789,171 | A | 8/1998 | Smeltzer |
| 5,795,717 | A | 8/1998 | Nakayama et al. |
| 5,798,336 | A | 8/1998 | Travis et al. |
| 5,801,234 | A | 9/1998 | Hodgson et al. |
| 5,807,673 | A | 9/1998 | Ohno et al. |
| 5,861,245 | A | 1/1999 | McClelland et al. |
| 5,925,517 | A | 7/1999 | Tyagi et al. |
| 5,958,736 | A | 9/1999 | St.ang.hl et al. |
| 5,994,066 | A | 11/1999 | Bergeron et al. |
| 5,994,847 | A | 11/1999 | Konopka |
| 6,001,564 | A | 12/1999 | Bergeron et al. |
| 6,015,666 | A | 1/2000 | Springer et al. |
| 6,130,091 | A | 10/2000 | Binz et al. |
| 6,156,507 | A | 12/2000 | Hiramatsu et al. |
| 6,174,670 | B1 | 1/2001 | Wittwer et al. |
| 6,218,110 | B1 | 4/2001 | Nakayama et al. |
| 6,299,879 | B1 | 10/2001 | Boden Wastfalt et al. |
| 6,376,186 | B1 | 4/2002 | Hogan et al. |
| 6,380,370 | B1 | 4/2002 | Doucette-Stamm et al. |
| 6,506,893 | B1 | 1/2003 | El Solh et al. |
| 6,534,284 | B1 | 3/2003 | El-Sherbeini et al. |
| 6,548,639 | B1 | 4/2003 | Frykberg et al. |
| 6,569,627 | B2 | 5/2003 | Wittwer et al. |
| 6,570,001 | B1 | 5/2003 | Solh et al. |
| 6,593,114 | B1 | 7/2003 | Kunsch et al. |
| 6,660,835 | B1 | 12/2003 | Otto et al. |
| 6,664,045 | B1 | 12/2003 | Hyldig-Nielsen et al. |
| 6,692,739 | B1 | 2/2004 | Patti et al. |
| 6,703,025 | B1 | 3/2004 | Patti et al. |
| 6,737,248 | B2 | 5/2004 | Kunsch et al. |
| 6,753,149 | B2 | 6/2004 | Bailey et al. |
| 6,764,823 | B2 | 7/2004 | Tomichi et al. |
| 6,803,044 | B1 | 10/2004 | Catania et al. |
| 6,838,435 | B1 | 1/2005 | Krijgsveld et al. |
| 6,887,846 | B2 | 5/2005 | Catania et al. |
| 6,936,422 | B2 | 8/2005 | El Solh et al. |
| 6,946,267 | B2 | 9/2005 | Liu et al. |
| 7,002,005 | B1 | 2/2006 | Berghof et al. |
| 7,045,131 | B2 | 5/2006 | Patti et al. |
| 7,049,122 | B2 | 5/2006 | Chang et al. |
| 7,060,458 | B1 | 6/2006 | Doucette-Stamm et al. |
| 7,067,135 | B2 | 6/2006 | Balaban |
| 7,070,962 | B1 | 7/2006 | Ryncarz |
| 7,074,415 | B2 | 7/2006 | Hamel et al. |
| 7,074,598 | B2 | 7/2006 | Cockerill, III et al. |
| 7,074,599 | B2 | 7/2006 | Uhl et al. |
| 7,098,023 | B1 | 8/2006 | Doucette-Stamm et al. |
| 7,101,969 | B1 | 9/2006 | Pelletier et al. |
| 2002/0055101 | A1 | 5/2002 | Bergeron et al. |
| 2002/0061569 | A1 | 5/2002 | Haselbeck et al. |
| 2002/0098492 | A1 | 7/2002 | Taya et al. |
| 2002/0137685 | A1 | 9/2002 | Catania et al. |
| 2002/0159997 | A1 | 10/2002 | Patti et al. |
| 2002/0168697 | A1 | 11/2002 | Tomich et al. |
| 2003/0049636 | A1 | 3/2003 | Bergeron et al. |
| 2003/0049648 | A1 | 3/2003 | Choi |
| 2003/0054436 | A1 | 3/2003 | Kunsch et al. |
| 2003/0064388 | A1 | 4/2003 | Nakayama et al. |
| 2003/0068625 | A1 | 4/2003 | Sheehan et al. |
| 2003/0082200 | A1 | 5/2003 | Ljungh et al. |
| 2003/0087864 | A1 | 5/2003 | Talbot et al. |
| 2003/0109019 | A1 | 6/2003 | Chang et al. |
| 2003/0153733 | A1 | 8/2003 | Simpson et al. |
| 2003/0158135 | A1 | 8/2003 | El Solh et al. |
| 2003/0176679 | A1 | 9/2003 | El Solh et al. |
| 2003/0180733 | A1 | 9/2003 | Bergeron et al. |
| 2003/0186364 | A1 | 10/2003 | Bailey et al. |
| 2003/0232337 | A1 | 12/2003 | Liu et al. |
| 2004/0023207 | A1* | 2/2004 | Polansky .......................... 435/5 |
| 2004/0029129 | A1 | 2/2004 | Wang et al. |
| 2004/0043037 | A1 | 3/2004 | Kunsch et al. |
| 2004/0063103 | A1 | 4/2004 | Uhl et al. |
| 2004/0101919 | A1 | 5/2004 | Hook et al. |
| 2004/0147734 | A1 | 7/2004 | Doucette-Stamm et al. |
| 2004/0185478 | A1 | 9/2004 | Bergeron et al. |
| 2004/0241824 | A1 | 12/2004 | Schrenzel et al. |
| 2004/0248089 | A1 | 12/2004 | Banada et al. |
| 2004/0254360 | A1 | 12/2004 | Raoult et al. |
| 2005/0019893 | A1 | 1/2005 | Huletsky et al. |
| 2005/0042606 | A9 | 2/2005 | Bergeron et al. |
| 2005/0123946 | A1 | 6/2005 | Snaidr et al. |
| 2005/0142575 | A1 | 6/2005 | Jannes et al. |
| 2005/0176001 | A1 | 8/2005 | Nakano et al. |
| 2005/0208560 | A1 | 9/2005 | El Solh et al. |
| 2005/0233345 | A1 | 10/2005 | Padmapriya et al. |
| 2006/0057613 | A1 | 3/2006 | Ramakrishnan et al. |
| 2006/0111300 | A1 | 5/2006 | Catania et al. |
| 2006/0115490 | A1 | 6/2006 | Masignani et al. |
| 2006/0115819 | A1 | 6/2006 | Claeys et al. |
| 2006/0140972 | A1 | 6/2006 | Alm et al. |
| 2006/0160121 | A1 | 7/2006 | Mounts et al. |
| 2006/0171964 | A1 | 8/2006 | Foster et al. |
| 2006/0177465 | A1 | 8/2006 | Hamel et al. |
| 2006/0194751 | A1 | 8/2006 | Meinke et al. |
| 2006/0199182 | A1 | 9/2006 | Drancourt et al. |
| 2006/0199200 | A1 | 9/2006 | Uhl et al. |
| 2006/0252078 | A1 | 11/2006 | Huletsky et al. |
| 2006/0263810 | A1 | 11/2006 | Bergeron et al. |
| 2007/0031866 | A1 | 2/2007 | Cockerill et al. |
| 2007/0082340 | A1 | 4/2007 | Huletsky et al. |

OTHER PUBLICATIONS

Brakstad, et al., "Multiplex Polymerase Chain Reaction for Detection of Genes for *Staphylococcus aureus* Thermonuclease and Methicilh Resistance and Correlation with Oxacillin Resistance", APMIS, 1993, vol. 101; pp. 681-688.

Becker-Andre, et al., "Absolute mRNA Quantification Using the Polymerase Chain Reaction (PCR). A Novel Approach by a PCR Aided Transcript titration assay (PATTY)." Nucleic Acids Research, 1989, vol. 17, No. 22; pp. 9437-9447.

Becker, et al., "Does Nasal Cocolonization by Methicillin—Resistant Coagulase-Negative Staphylococci and Methicillin-Susceptible *Staphylococcus aureus* Strains Occur Frequently Enough to Represent a Risk of False-Positive Methicillin-Resistant *S. aureus* Determination by Molecular Methods?" J. Clin Microbiol., Jan. 2006, vol. 44, No. 1; pp. 229-231.

Corkill, et al. "Detection of Elements of Staphylococcal Cassette Chromosome (SCC) in Methicillin-susceptible (mecA gene negative) Homologue of Fucidin-Resistant MRSA", J. Antimicrobial Chemotherapy. May 18, 2004, vol. 54; pp. 229-231.

Cuny, C., et al., "PCR for the Identification of Methicillin-Resistant *Staphylococcus aureus* (MRSA) Strains Using a Single Primer Pair Specific for SCCmec Elements and the Neighbor in Chromosome-Boprne orfX." Clinical Microbiology and Infectious Diseases, 2005, vol. 11; pp. 834-837.

Deplano, et al., "In vivo Deletion of the Methicillin Resistance mec Region from the Chromosome of *Staphylococcus aureus* Strains" J. Antimicrobial Chemotherapy, 2000, vol. 46; pp. 617-620.

Diekema, et al., "Survey of Infections due to *Staphylococcus* Species: Frequency of Occurrence and Antimicrobial Susceptibility of Isolates Collected in the United States, Canada, Latin America, Europe, and the Western Pacific Region for the SENTRY Antimicrobial Surveillance Program." Clin. Infect. Dis., 2001 32(Suppl. 2):S114-S132.

Diviacco, et al., "A Novel Procedure for Quantitative Polymerase Chain Reaction by Coamplification of Competitive Templates." Gene, 1992, vol. 122; pp. 313-320.

(56) References Cited

OTHER PUBLICATIONS

Freeman, et al., "Quantitative RT-PCR: Pitfalls and Potential," Biotechniques, 1999, vol. 26, No. 1; pp. 112-125.
GeneBank GI: 46993 [online] Jan. 21, 1991.
GeneBank GI:2988485 [online] Mar. 26, 1998.
Grisold, et al., "Detection of Methicillin-Resistant *Staphylococcus aureus* and Simultaneous Confirmation by Automated Nucleic Acid Extraction and Real-Time PCR." Journal of Clinical Microbiology, Jul. 2002, vol. 40, No. 7; pp. 2392-2397.
Hagen, R. M., et al., "Development of a Real-Time PCR Assay for Rapid Identification of Methicillin-Resistant *Staphylococcus aureus* from Clinical Samples." International Journal of Medical Microbiology, 2005, vol. 295m; pp. 77-86.
Handwerger, et al., "Identification of Chromosomal Mobile Element Conferring High-Level Vancomycin Resistance in *Enterococcus faecium*." Antimicrobial Agents and Chemotherapy, Nov. 1995, vol. 39, No. 11, pp. 2446-2453.
Hanssen, et al., "Local Variants of Staphylococcal Cassette Chromosome mec in Sporadtic Methicillin-Resistant *Staphylococcus aureus* and Methicillin-Resistant Coagulase-Negatiive Staphylococci: Evidence of Horizontal Gene Transfer?"Antimicrobial, Agents and Chemotherapy, Jan. 2004, vol. 48, No. 1; pp. 285-296.
Huletsky, A., et al., "Identification of Methicillin-Resistant *Staphylococcus aureus* Carriage in Less than 1 Hour during a Hospital Surveillance Program", Clinical Infectious Diseases, Apr. 1, 2005, vol. 40; pp. 976-981.
Huletsky, et al., "New Real-Time PCR Assay for Rapid Detection of Methicillin-Resistant *Staphylococcus aureus* Directly from Specimens Containing a Mixture of Staphylococci." J. Clin. Microbiol., May 2004 vol. 42, No. 5; pp. 1875-1884.
Hiramatsu, et al., "Genetic Basis for Molecular Epidemiology of MRSA." J. Infect. Chemotherapy, 1996, vol. 2; pp. 117-129.
Ito, T., et al., "Novel Type V Staphylococcal Casetter Chromosome mec Driven by a Novel Casete Chromosome Recombinase ccrC." Antimicrobial Agents in Chemotherapy, 2004, vol. 48; pp. 2637-2651.
Ito, T., et al., "Insights on Antibiotic Resistance of *Staphylococcus aureus* from its Whole Genome: Genomic Island SCC." Drug Resistance, 2003, Update 6; pp. 41-52.
Ito, et al., "Structural Comparison of Three Types of Staphylococcal Cassette Chromosome mec Integrated in the Chromosome in Methicillin-Resistant *Staphylococcus aureus*."Antimicrobial Agents and Chemotherapy, May 2001, vol. 45, No. 5; pp. 1323-1336.
Launay, et al., "Transfer of Vancomycin Resistance Transposon Tn1549 from *Clostridium symbiosum* to *Enterococcus* spp. in the Gut of Gnotobiotic Mice." Antimicrobial Agents and Chemotherapy, Mar. 2006, vol. 50, No. 3; pp. 1054-1062.
Lina, et al., "Involvement of Panton-Valentine Leukocidin-Producing *Staphylococcus aureus* in Primary Skin Infections and Pneumonia." Clinical Infect. Dis., 1999, vol. 29; pp. 1128-1132.
Louie, L., et al., "Rapid Detection of Methicillin-resistant staphylococci from Blood Culture Bottles by using Multiplex PCR Assay", Journal of Clinical Microbiology, (Aug. 1, 2002), vol. 40, No. 8; pp. 2786-2790.
Ma, et al., "Novel Type of Staphylococcal Cassette Chromosome mec Identified in Community-Acquired Methicillin-Resistant *Staphylococcus aureus* Strains." Antimicrobial Agents and Chemotherapy, Apr. 2002, vol. 46, No. 4; pp. 1147-1152.
Mackay, et al., "Survey and Summary Real-Time PCR in Virology." Nucleic Acids Research, 2002, vol. 30, No. 6; pp. 1292-1305.
Matsuhashi, et al., FEBS Letters, "Evolution of an Inducible Penicillin-target Protein in Methicillin-resistant *Staphylococcus aureus* by Gene Fusion" 1987, vol. 221; pp. 167-171.
Reischl, et al., "Rapid Identification of Methicillin-Resistant *Staphylococcus aures* and Simultaneous Species Confirmation Using Real-Time Fluorescence PCR,." J. Clin. Microbiol., Jun. 2000, vol. 38, No. 6; pp. 2429-2433.
Roth, et al., "Use of an Oligonucleotide Array for Laboratory Diagnosis of Bacteria Responsible for Acute Upper Respiratory Infections" J. Clin. Microbiol., Sep. 2004, vol. 42, No. 9; pp. 4268-4274.
Rupp, et al., "Be Aware of the Possibility of False-Positive Results in Single-Locus PCR Assays for Methicillin-Resistant *Staphylococcus aureus*." Clinical Microbiology, Jun. 2006, vol. 44, No. 6; p. 2317.
Sundsfjord, et al., "Genetic Methods for Detection of Antimicrobial Resistance." APMIS, 2004, vol. 112; pp. 815-837.
Toleman, et al., "Common Regions e.g. orf513 and Antibiotic Resistance: IS91-like Elements Evolving Complex Class 1 integrons." Journal of Antimicrobial Chemotherapy, Jun. 2, 2006, vol. 58; pp. 1-6.
Tyagi, et al., "Multicolor Molecular Beacons for Allele Discrimination." Nature Biotechnology, Jan. 1998, vol. 16, pp. 49-53.
Ubukata, K., et al., "Rapid Detection of the mecA Gene in Methicillin-Resistant Staphylococci by Enzymatic Detection of Polymerase Chain Reaction Products", Journal of Clinical Microbiology, 1992, vol. 30; p. 1728.
Ubukata, K., et al., "Homology of mecA Gene in methicillin-Resistant *Staphylococcus haemolyticus* and *Staphylococcus simulans* to that of *Staphylococcus aureus*." Journal: Antimicrobial Agents Chemotherapy, Jan. 1990, vol. 34, No. 1; pp. 170-172.
Unal, S., et al., "Detection of Methicillin-Resistant Staphylococci by Using the Polymerase Chain Reaction", Journal of Clinical Microbiology, 1992, vol. 30; p. 1685.
Vannuffel, P., et al., "Specific Detection of Methicillin-resistant *Staphylococcus* Species by Multiplex PCR", (Nov. 1, 1995), vol. 33, No. 11; pp. 2864-2867.
Warren, et al., "Detection of Methicillin-Resistant *Staphylococcus aureus* Directly from Nasal Swab Specimens by a Real-Time PCR Assay." J. Clin. Microbiol., Dec. 2004, vol. 42, No. 12: pp. 5578-5581.
Witte, et al., "Emergence of Methicillin-Resistant *Staphylococcus aureus* with Panton-Valentine Leukocidin Genes in Central Europe." Eur J. Microbiology and Infectious Diseases, 2002, vol. 24; pp. 1-5.
Zimmerman, et al., "Technical Aspects of Quantitative Competitive PCR." Biotechniques, 1996, vol. 21, No. 2; pp. 268-279.

\* cited by examiner

FIGURE 1

| SEQ ID | Name | PRIMER SEQUENCES | Length |
|---|---|---|---|
| SEQ ID NO: 1 | orfX | 5'-FAM-TCGTCATTGGCGGATCAAACGGC-BHQ1-3' | 23 |
| SEQ ID NO: 2 | orfX-F | CGCATGACCCAAGGGCA | 17 |
| SEQ ID NO: 3 | mecii619 | ATTTCATATATGTAATTCCTCCACATCTC | 29 |
| SEQ ID NO: 4 | mec574 | GTCAAAAATCATGAACCTCATTACTTATG | 29 |
| SEQ ID NO: 5 | mecv492 | CTCTGCTTTATATTATAAAATTACGGCTG | 29 |
| SEQ ID NO: 6 | mec vii512 | CACTTTTTATTCTTCAAAGATTTGAGC | 27 |
| SEQ ID NO: 7 | 511-108 | TGGAAATCCATCTCTACTTTATTGTTT | 27 |
| SEQ ID NO: 8 | 511-114 | TCCATCTCTACTTTATTGTTTTCTTCAA | 27 |
| SEQ ID NO: 9 | MecA | 5'-YAKY-CTGATTCAGGTTACGGACAAGGT-BHQ1-3' | 23 |
| SEQ ID NO: 10 | Mec-F | GGTGAAGATATACCAAGTGATTA | 23 |
| SEQ ID NO: 11 | Mec-R | GTGAGGTGCGTTAATATTGC | 20 |
| SEQ ID NO: 12 | Sa442 | 5'-ROX-TACATACAGAACAATGTTTCCGATGCAA-BHQ2-3' | 28 |
| SEQ ID NO: 13 | Sa442-F | GTCGGTACACGATATTCTTCACG | 23 |
| SEQ ID NO: 14 | Sa442-R | CTCTCGTATGACCAGCTTCGGTAC | 24 |
| SEQ ID NO: 15 | HuGlob | 5'-Cy5-CCTGAGGAGAAGTCTGCCGTTACTGC-IABRQSp-3' | 26 |
| SEQ ID NO: 16 | HuGlob-F | CTGACACAACTGTGTTCACTAGC | 23 |
| SEQ ID NO: 17 | HuGlob-R | CCACATGCCCAGTTTCTATTG | 21 |
| SEQ ID NO: 18 | Nuc-F | AAGCGATTGATGGTGATACG | 20 |
| SEQ ID NO: 19 | Nuc-R | AAATGCACTTGCTTCAGGAC | 20 |
| SEQ ID NO: 20 | Nuc-P | 5'-ROX-GTTGATACACCTGAAACAAAGCATCCTAAAAAAGGTGBHQ2-3' | 37 |
| SEQ ID NO: 21 | HHB-F | ACA CAA CTG TGT TCA CTA GC | 20 |
| SEQ ID NO: 22 | HHB-R | CAA CTT CAT CCA CGT TCA CC | 20 |
| SEQ ID NO: 23 | HHB-P | 5'-HEX-CCA CAG GGC AGT AAC GGC AGA CT-BHQ2-3' | 23 |
| SEQ ID NO: 24 | OrfX-Ra | TGAACGTGGATTTAATGTCCACC | 23 |
| SEQ ID NO: 25 | Van-1 | GCTATGGCAGTTTTCCGTGTG | 21 |
| SEQ ID NO: 26 | Van-2 | AACGCTTCTTCATGGCTCTTG | 21 |
| SEQ ID NO: 27 | Van-3 | TGCCGGAAAAGCCCGGAAACACG | 24 |
| SEQ ID NO: 28 | Van-4 | AGAAATGGAACGGCTGGCAGC | 22 |
| SEQ ID NO: 29 | Van-5 | GAGGGGGAAATGGTGAGAGGT | 22 |
| SEQ ID NO: 30 | Van-6 | TTCCAATATCACCATGACGCTG | 22 |
| SEQ ID NO: 31 | Van-7 | GCTGCGGAGCTTTGAATATC | 20 |
| SEQ ID NO: 32 | Van-8 | CGTGTGCTGCAGGATACTAC | 20 |
| SEQ ID NO: 33 | Van-9 | TGCATCAGCCCGTTCAAACGCC | 21 |
| SEQ ID NO: 34 | Van-10 | CGCGTTTACGGTGTCGTATTC | 20 |
| SEQ ID NO: 35 | Van-11 | TGCGGCTCAATCCGAAAGTAG | 21 |
| SEQ ID NO: 36 | Van-12 | TGCGAAATGCCCGTATTTCCGG | 22 |
| SEQ ID NO: 37 | Van-13 | TGAGAGCTCAGGAGGCTGCATTATGAACCATG | 32 |
| SEQ ID NO: 38 | Van-14 | ATGTCTAGAGTCAGGCTGCCAGCCGTTCC | 29 |

FIGURE 4
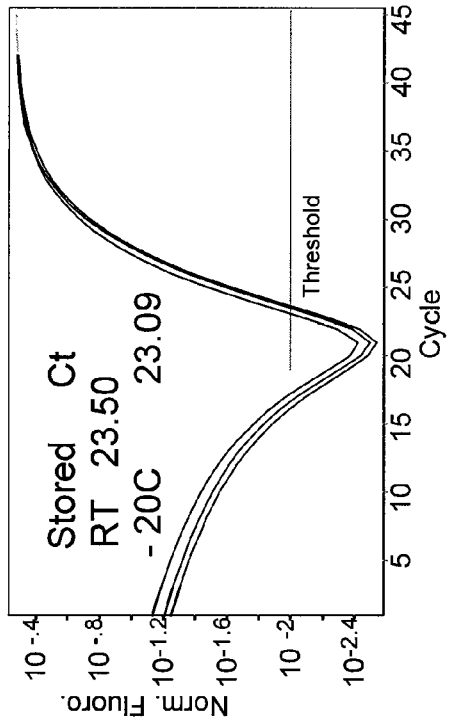
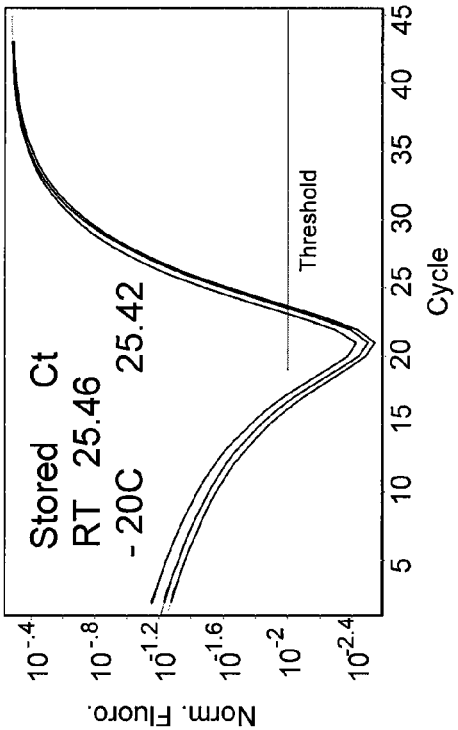
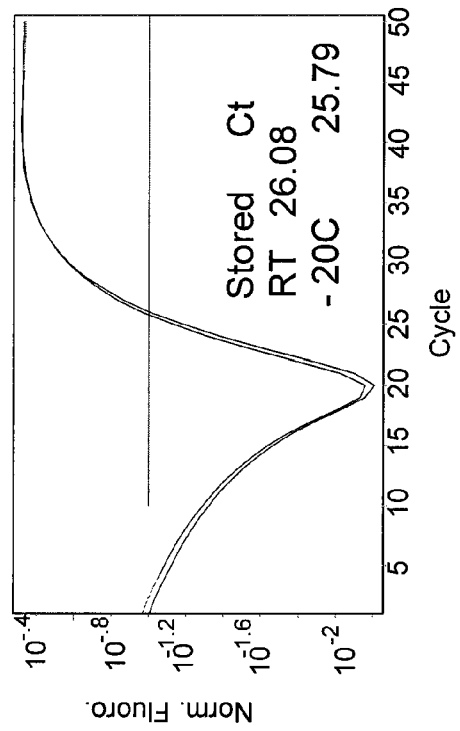

SEQUENCE LISTING

```
<160> NUMBER OF SEQ ID NOS: 38

<210> SEQ ID NO 1
<211> LENGTH: 23
<212> TYPE: DNA
<213> ORGANISM: Artificial Sequence
<220> FEATURE:
<223> OTHER INFORMATION: Primer orfX

<400> SEQUENCE: 1
tcgtcattgg cggatcaaac ggc                                          23

<210> SEQ ID NO 2
<211> LENGTH: 17
<212> TYPE: DNA
<213> ORGANISM: Artificial Sequence
<220> FEATURE:
<223> OTHER INFORMATION: Primer orfX-F

<400> SEQUENCE: 2
cgcatgaccc aagggca                                                 17

<210> SEQ ID NO 3
<211> LENGTH: 29
<212> TYPE: DNA
<213> ORGANISM: Artificial Sequence
<220> FEATURE:
<223> OTHER INFORMATION: Primer mecii519

<400> SEQUENCE: 3
atttcatata tgtaattcct ccacatctc                                    29

<210> SEQ ID NO 4
<211> LENGTH: 29
<212> TYPE: DNA
<213> ORGANISM: Artificial Sequence
<220> FEATURE:
<223> OTHER INFORMATION: Primer meci574

<400> SEQUENCE: 4
gtcaaaaatc atgaacctca ttacttatg                                    29

<210> SEQ ID NO 5
<211> LENGTH: 29
<212> TYPE: DNA
<213> ORGANISM: Artificial Sequence
<220> FEATURE:
<223> OTHER INFORMATION: Primer mecv492

<400> SEQUENCE: 5
ctctgcttta tattataaaa ttacggctg                                    29
```

```
<210> SEQ ID NO 6
<211> LENGTH: 27
<212> TYPE: DNA
<213> ORGANISM: Artificial Sequence
<220> FEATURE:
<223> OTHER INFORMATION: Primer mec vii512

<400> SEQUENCE: 6 cacttttat tcttcaaaga tttgagc                                         27

<210> SEQ ID NO 7
<211> LENGTH: 27
<212> TYPE: DNA
<213> ORGANISM: Artificial Sequence
<220> FEATURE:
<223> OTHER INFORMATION: Primer 511-108 for detection of MREJ Type IV

<400> SEQUENCE: 7
tggaaatcca tctctacttt attgttt                                        27

<210> SEQ ID NO 8
<211> LENGTH: 28
<212> TYPE: DNA
<213> ORGANISM: Artificial Sequence
<220> FEATURE:
<223> OTHER INFORMATION: Primer 511-114 for detection of MREJ Type IV

<400> SEQUENCE: 8
tccatctcta ctttattgtt ttcttcaa                                       28

<210> SEQ ID NO 9
<211> LENGTH: 23
<212> TYPE: DNA
<213> ORGANISM: Artificial Sequence
<220> FEATURE:
<223> OTHER INFORMATION: Primer MecA

<400> SEQUENCE: 9
ctgattcagg ttacggacaa ggt                                            23

<210> SEQ ID NO 10
<211> LENGTH: 23
<212> TYPE: DNA
<213> ORGANISM: Artificial Sequence
<220> FEATURE:
<223> OTHER INFORMATION: Primer Mec-F

<400> SEQUENCE: 10
ggtgaagata taccaagtga tta                                            23

<210> SEQ ID NO 11
<211> LENGTH: 20
<212> TYPE: DNA
<213> ORGANISM: Artificial Sequence
<220> FEATURE:
<223> OTHER INFORMATION: Primer Mec-R

<400> SEQUENCE: 11
gtgaggtgcg ttaatattgc                                                20

<210> SEQ ID NO 12
<211> LENGTH: 28
<212> TYPE: DNA
<213> ORGANISM: Artificial Sequence
<220> FEATURE:
<223> OTHER INFORMATION: Primer Sa442

<400> SEQUENCE: 12
```
tacatacaga acaatgtttc cgatgcaa                                      28

<210> SEQ ID NO 13
<211> LENGTH: 23
<212> TYPE: DNA
<213> ORGANISM: Artificial Sequence
<220> FEATURE:
<223> OTHER INFORMATION: Primer Sa442-F

<400> SEQUENCE: 13
gtcggtacac gatattcttc acg                                           23

<210> SEQ ID NO 14
<211> LENGTH: 24
<212> TYPE: DNA
<213> ORGANISM: Artificial Sequence
<220> FEATURE:
<223> OTHER INFORMATION: Primer Sa442-R

<400> SEQUENCE: 14
ctctcgtatg accagcttcg gtac                                          24

<210> SEQ ID NO 15
<211> LENGTH: 26
<212> TYPE: DNA
<213> ORGANISM: Artificial Sequence
<220> FEATURE:
<223> OTHER INFORMATION: Primer HuGlob

<400> SEQUENCE: 15
cctgaggaga agtctgccgt tactgc                                        26

<210> SEQ ID NO 16
<211> LENGTH: 23
<212> TYPE: DNA
<213> ORGANISM: Artificial Sequence
<220> FEATURE:
<223> OTHER INFORMATION: Primer HuGlob-F

<400> SEQUENCE: 16
ctgacacaac tgtgttcact agc                                           23

<210> SEQ ID NO 17
<211> LENGTH: 21
<212> TYPE: DNA
<213> ORGANISM: Artificial Sequence
<220> FEATURE:
<223> OTHER INFORMATION: Primer HuGlob-R

<400> SEQUENCE: 17
ccacatgccc agtttctatt g                                             21

<210> SEQ ID NO 18
<211> LENGTH: 20
<212> TYPE: DNA
<213> ORGANISM: Artificial Sequence
<220> FEATURE:
<223> OTHER INFORMATION: Primer Nuc-F

<400> SEQUENCE: 18
aagcgattga tggtgatacg                                               20

<210> SEQ ID NO 19
<211> LENGTH: 20
<212> TYPE: DNA
<213> ORGANISM: Artificial Sequence

```
<220> FEATURE:
<223> OTHER INFORMATION: Primer Nuc-R

<400> SEQUENCE: 19
aaatgcactt gcttcaggac                                                    20

<210> SEQ ID NO 20
<211> LENGTH: 37
<212> TYPE: DNA
<213> ORGANISM: Artificial Sequence
<220> FEATURE:
<223> OTHER INFORMATION: Primer Nuc-P

<400> SEQUENCE: 20
gttgatacac ctgaaacaaa gcatcctaaa aaaggtg                                 37

<210> SEQ ID NO 21
<211> LENGTH: 20
<212> TYPE: DNA
<213> ORGANISM: Artificial Sequence
<220> FEATURE:
<223> OTHER INFORMATION: Primer HHB-F

<400> SEQUENCE: 21
acacaactgt gttcactagc                                                    20

<210> SEQ ID NO 22
<211> LENGTH: 20
<212> TYPE: DNA
<213> ORGANISM: Artificial Sequence
<220> FEATURE:
<223> OTHER INFORMATION: Primer HHB-R

<400> SEQUENCE: 22
caacttcatc cacgttcacc                                                    20

<210> SEQ ID NO 23
<211> LENGTH: 23
<212> TYPE: DNA
<213> ORGANISM: Artificial Sequence
<220> FEATURE:
<223> OTHER INFORMATION: Primer HHB-P

<400> SEQUENCE: 23
ccacagggca gtaacggcag act                                                23

<210> SEQ ID NO 24
<211> LENGTH: 23
<212> TYPE: DNA
<213> ORGANISM: Artificial Sequence
<220> FEATURE:
<223> OTHER INFORMATION: Primer OrfX-Ra

<400> SEQUENCE: 24
tgaacgtgga tttaatgtcc acc                                                23

<210> SEQ ID NO 25
<211> LENGTH: 21
<212> TYPE: DNA
<213> ORGANISM: Artificial Sequence
<220> FEATURE:
<223> OTHER INFORMATION: Primer Van-1

<400> SEQUENCE: 25
gctatggcag ttttccgtgt g                                                  21
```

```
<210> SEQ ID NO 26
<211> LENGTH: 21
<212> TYPE: DNA
<213> ORGANISM: Artificial Sequence
<220> FEATURE:
<223> OTHER INFORMATION: Primer Van-2

<400> SEQUENCE: 26
aacgcttctt catggctctt g                                              21

<210> SEQ ID NO 27
<211> LENGTH: 23
<212> TYPE: DNA
<213> ORGANISM: Artificial Sequence
<220> FEATURE:
<223> OTHER INFORMATION: Primer Van-3

<400> SEQUENCE: 27
tgccggaaaa gcccggaaac acg                                            23

<210> SEQ ID NO 28
<211> LENGTH: 21
<212> TYPE: DNA
<213> ORGANISM: Artificial Sequence
<220> FEATURE:
<223> OTHER INFORMATION: Primer Van-4

<400> SEQUENCE: 28
agaaatggaa cggctggcag c                                              21

<210> SEQ ID NO 29
<211> LENGTH: 21
<212> TYPE: DNA
<213> ORGANISM: Artificial Sequence
<220> FEATURE:
<223> OTHER INFORMATION: Primer Van-5

<400> SEQUENCE: 29 gaggggggaaa tggtgagagg t                                             21

<210> SEQ ID NO 30
<211> LENGTH: 22
<212> TYPE: DNA
<213> ORGANISM: Artificial Sequence
<220> FEATURE:
<223> OTHER INFORMATION: Primer Van-6

<400> SEQUENCE: 30
ttccaatatc accatgacgc tg                                             22

<210> SEQ ID NO 31
<211> LENGTH: 20
<212> TYPE: DNA
<213> ORGANISM: Artificial Sequence
<220> FEATURE:
<223> OTHER INFORMATION: Primer Van-7

<400> SEQUENCE: 31
gctgcggagc tttgaatatc                                                20

<210> SEQ ID NO 32
<211> LENGTH: 20
<212> TYPE: DNA
<213> ORGANISM: Artificial Sequence
<220> FEATURE:
<223> OTHER INFORMATION: Primer Van-8

<400> SEQUENCE: 32
```

```
cgtgtgctgc aggatactac                                                  20

<210> SEQ ID NO 33
<211> LENGTH: 21
<212> TYPE: DNA
<213> ORGANISM: Artificial Sequence
<220> FEATURE:
<223> OTHER INFORMATION: Primer Van-9

<400> SEQUENCE: 33
tgcatcagcc gttcaaacgc c                                                21

<210> SEQ ID NO 34
<211> LENGTH: 21
<212> TYPE: DNA
<213> ORGANISM: Artificial Sequence
<220> FEATURE:
<223> OTHER INFORMATION: Primer Van-10

<400> SEQUENCE: 34
cgcgtttacg gtgtcgtatt c                                                21

<210> SEQ ID NO 35
<211> LENGTH: 21
<212> TYPE: DNA
<213> ORGANISM: Artificial Sequence
<220> FEATURE:
<223> OTHER INFORMATION: Primer Van-11

<400> SEQUENCE: 35
tgcggctcaa tccgaaagta g                                                21

<210> SEQ ID NO 36
<211> LENGTH: 22
<212> TYPE: DNA
<213> ORGANISM: Artificial Sequence
<220> FEATURE:
<223> OTHER INFORMATION: Primer Van-12

<400> SEQUENCE: 36
tgcgaaatgc ccgtatttcc gg                                               22

<210> SEQ ID NO 37
<211> LENGTH: 32
<212> TYPE: DNA
<213> ORGANISM: Artificial Sequence
<220> FEATURE:
<223> OTHER INFORMATION: Primer Van-13

<400> SEQUENCE: 37
tgagagctca ggaggctgca ttatgaacca tg                                    32

<210> SEQ ID NO 38
<211> LENGTH: 29
<212> TYPE: DNA
<213> ORGANISM: Artificial Sequence
<220> FEATURE:
<223> OTHER INFORMATION: Primer Van-14

<400> SEQUENCE: 38
atgtctagag tcaggctgcc agccgttcc                                        29
```

METHODS, COMPOSITIONS AND KITS FOR DETECTION AND ANALYSIS OF ANTIBIOTIC-RESISTANT BACTERIA

CROSS-REFERENCE TO RELATED APPLICATIONS

The present application is a continuation of application of U.S. application Ser. No. 13/229,598, filed Sep. 9, 2011, which is a continuation of U.S. application Ser. No. 13/205, 496, filed Aug. 8, 2011, which is a continuation of U.S. application Ser. No. 13/178,807, filed on Jul. 8, 2011, which is a continuation of U.S. application Ser. No. 13/038,035, filed Mar. 1, 2011, which is a continuation application of U.S. application Ser. No. 12/106,137, filed Apr. 18, 2008, now U.S. Pat. No. 8,017,337, which claims the benefit of the filing date of U.S. Provisional Patent Application Ser. No. 60/907, 848, filed Apr. 19, 2007. All applications to which priority is claimed are hereby incorporated by reference in their entirety for all purposes.

FIELD OF THE INVENTION

The present invention relates generally to detection of antibiotic-resistant bacteria in a sample. In particular, the invention provides methods, compositions and kits for detecting and analyzing methicillin-resistant Staphylococcus aureus (MRSA) and other methicillin-resistant bacteria in a sample.

BACKGROUND OF THE INVENTION

New strains and species of antibiotic-resistant bacteria are becoming increasingly common in hospitals and other healthcare facilities. Treatment options for infections caused by such bacteria are often limited to costly medications that produce undesirable side effects. Antibiotic resistance has been detected in strains of a number of bacteria, including *Staphylococcus aureus, Oerskovia turbata, Aracanobacterium haemolyticum, Streptococcus bovis, Streptococcus gallolyticus, Streptococcus lutetiensis, Bacillus circulans, Paenibacillus, Rhodococcus, Enterococcus, Klebsiella*, as well as anaerobic bacteria belonging to the *Clostridium* genus and *Eggerthella lenta*, and many other pathogenic bacteria.

Methicillin-resistant *Staphylococcus aureus* (MRSA) is one example of a type of antibiotic-resistant bacteria emerging as a major epidemiological problem in hospitals throughout the world. MRSA strains are resistant to beta-lactams including penicillins, cephalosporins, carbapenems, and monobactams, which are the most commonly used antibiotics to cure *S. aureus* infections. Thus, MRSA infections can only be treated with toxic and costly antibiotics (such as Vancomycin and Linezolid), which, due in large part to their negative side effects, are normally only used as a last line of defense. A recent development in MRSA evolution is the emergence of strains that are at least partially resistant to such last-line antibiotics. If these partially resistant strains become fully resistant, there will be no effective treatment for infections caused by those strains.

Early detection and treatment are the primary tools for mitigating the transmission of constantly evolving strains of antibiotic-resistant bacteria. Traditional methods of screening for such bacteria require at least 2-4 days for results, during which time the infection has ample opportunity to spread. Rapid and accurate methods, compositions and kits for the detection of antibiotic-resistant bacteria are therefore essential for minimizing their transmission and the pace of their evolution.

SUMMARY OF THE INVENTION

Accordingly, the present invention provides methods, compositions and kits for rapid detection of antibiotic-resistant bacteria, including in one non-limiting embodiment, methicillin-resistant bacteria.

In one aspect, the invention provides a method of detecting methicillin-resistant *S. aureus* (MRSA) in a sample. In this aspect, the method includes the steps: (i) providing a first set of primers where the primers are complementary to at least a portion of a mecA polynucleotide sequence; (ii) providing a second set of primers, where the primers are complementary to at least a portion of a bridging region; (iii) providing a third set of primers, where the primers are complementary to at least a portion of an *S. aureus*-specific polynucleotide sequence, and where the *S. aureus*-specific polynucleotide sequence is not an orfX polynucleotide; (iv) combining the first, second and third set of primers with the sample in a reaction mixture; (v) performing a multi-cycle amplification reaction with the reaction mixture; and (vi) determining cycle numbers of appearance of each of the mecA, bridging region and *S. aureus*-specific polynucleotide sequences. In this aspect, the cycle numbers indicate whether MRSA is present in a sample.

In another aspect, the invention provides a method of detecting methicillin-resistant *S. aureus* (MRSA) in a sample. In this aspect, the method includes the steps: (i) determining whether a mecA polynucleotide is present in the sample; (ii) determining whether a bridging region polynucleotide is present in the sample; and (iii) determining whether an *S. aureus*-specific polynucleotide is present in the sample. In this aspect, the *S. aureus*-specific polynucleotide is not an orfX polynucleotide. In this aspect, if the mecA polynucleotide, the bridging region polynucleotide, and the *S. aureus*-specific polynucleotide are all present in said sample, then MRSA is present in said sample.

In still another aspect, the invention provides a method of detecting methicillin-resistant *S. aureus* (MRSA) in a sample. In this aspect, the method includes the steps: (i) providing a first set of primers, where the first set of primers are complementary to at least a portion of a mecA polynucleotide sequence; (ii) providing a second set of primers, where the second set of primers are complementary to at least a portion of an MSSA-orfX polynucleotide sequence; (iii) providing a third set of primers, where the third set of primers are complementary to at least a portion of an *S. aureus*-specific polynucleotide sequence, and where the *S. aureus*-specific polynucleotide sequence is not an orfX polynucleotide; (iv) combining the first, second and third set of primers with the sample in a reaction mixture; (v) performing a multi-cycle amplification reaction with said reaction mixture; and (vi) determining cycle numbers of appearance of each of the mecA, MSSA-orfX and *S. aureus*-specific polynucleotide sequences. In this aspect, the cycle numbers indicate whether MRSA is present in a sample.

In still another aspect, the invention provides a method of identifying bacteria in a sample. This method includes the steps: (i) determining whether a mecA polynucleotide is present in the sample; (ii) determining whether an MSSA-orfX polynucleotide is present in the sample; and (iii) determining whether an *S. aureus*-specific polynucleotide is present in the sample, where the *S. aureus*-specific polynucleotide is not an orfX polynucleotide. In this aspect, the combination of (a), (b), and (c) present in the sample identifies bacteria in the sample.

In one aspect, the invention provides a kit for identifying MRSA in a sample. Such a kit includes: a first set of primers complementary to at least a portion of a mecA polynucleotide sequence; a second set of primers complementary to at least a portion of MSSA-orfX polynucleotide sequence; a third set of primers complementary to at least a portion of an *S. aureus*-specific polynucleotide sequence, wherein said *S. aureus*-specific polynucleotide sequence is not a bridging sequence; and at least one member selected from: a DNA polymerase enzyme, dNTPs, magnesium and a stabilizer.

In another aspect, the invention provides a kit for identifying MRSA in a sample, and such a kit can include: a first set of primers complementary to at least a portion of a mecA polynucleotide sequence; a second set of primers complementary to at least a portion of a bridging sequence; a third set of primers complementary to at least a portion of an *S. aureus*-specific polynucleotide sequence, wherein said *S. aureus*-specific polynucleotide sequence is not a bridging sequence; and at least one member selected from: a DNA polymerase enzyme, dNTPs, magnesium and a stabilizer.

In one aspect, the invention provides method of detecting an antibiotic-resistant bacterial strain in a sample. This method can include the steps: (i) providing a first set of primers, which are capable of producing a first amplification product from at least a portion of a gene that confers antibiotic-resistance; (ii) providing a second set of primers, which are capable of producing a second amplification product from at least a portion of a bridging region; (iii) providing a third set of primers, which are capable of producing a third amplification product from at least a portion of a bacterial strain-specific polynucleotide sequence; (iv) combining the first, second and third set of primers with said sample in a reaction mixture; (v) performing a multi-cycle amplification reaction with the reaction mixture; and (vi) determining cycle numbers of appearance of each of the first, second and third amplification products. In this aspect, the cycle numbers indicate whether an antibiotic-resistant bacterial strain is present in the sample.

BRIEF DESCRIPTION OF THE FIGURES

FIG. 1 is a table listing sequences for primers and probes used in assays of the invention.

FIG. 4 illustrates results from a Real Time-PCR assay of stabilized PCR reaction mixes of the invention.

DETAILED DESCRIPTION OF THE PREFERRED EMBODIMENTS

Figure 2:
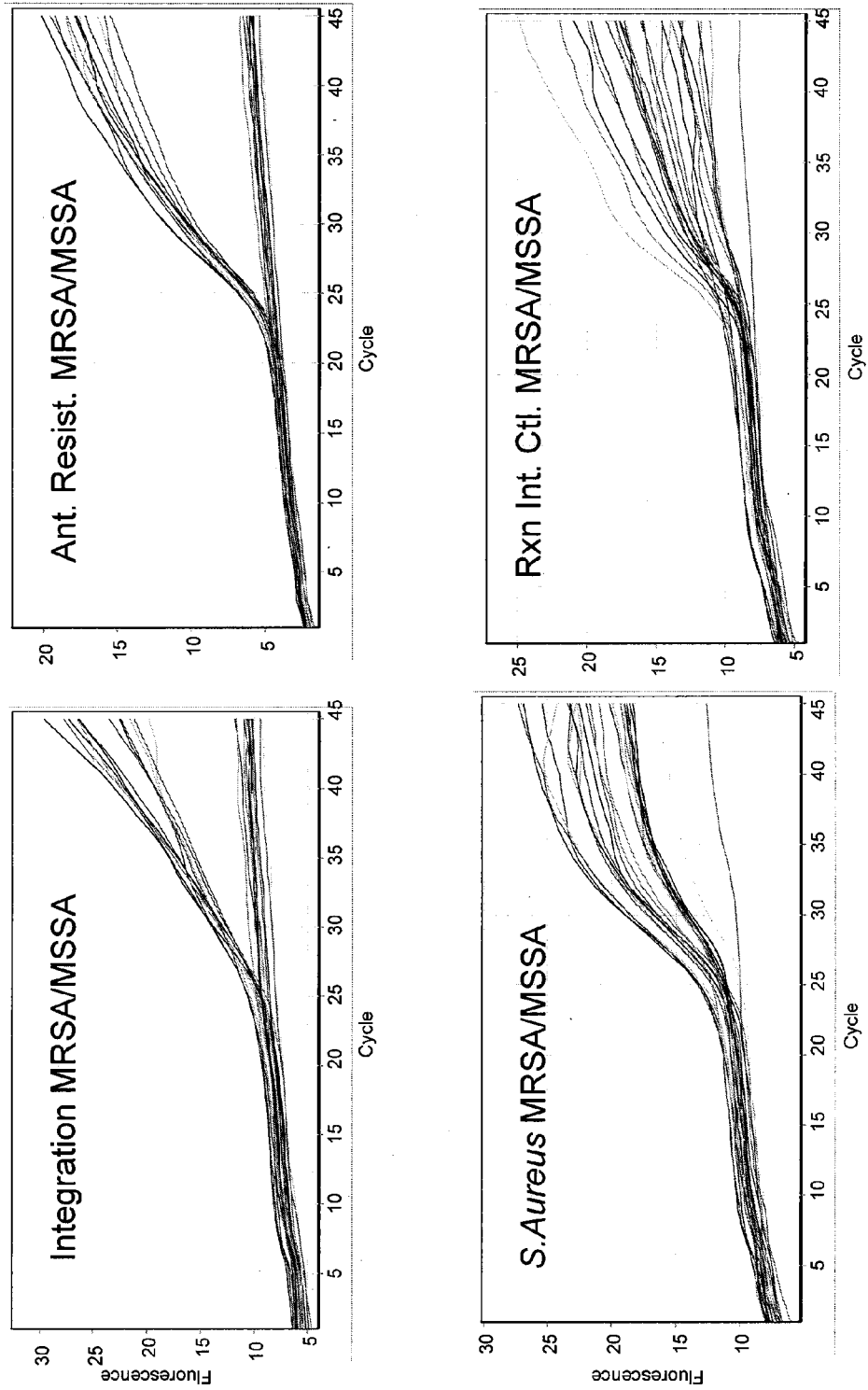
FIG. 2 illustrates results for detection of and discrimination between methicillin resistant *Staphylococcus aureus* (MRSA) and methicillin sensitive *Staphylococcus aureus* (MSSA) using methods of the invention.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention. It will be apparent to one of skill in the art that these additional features are also encompassed by the present invention.

Abbreviations

"MRSA" refers to "methicillin-resistant *Staphylococcus aureus*".

"MSSA" refers to "methicillin-susceptible *Staphylococcus aureus*".

Scc:orfX refers to a region between the SCCmec insertion cassette and the orfX region of the *S. aureus* genome. This region is also referred to as the "bridging region".

Definitions

The term "primer" refers to an oligonucleotide, either natural or synthetic, that is capable, upon forming a duplex with a polynucleotide (i.e. DNA) template, of acting as a point of initiation of nucleic acid synthesis and being extended from one end along the template so that an extended double strand (duplex) is formed. Primers of the invention may or may not be detectably labeled.

A "probe" is an oligonucleotide, either natural or synthetic, that is generally detectably labeled and used to identify complementary nucleic acid sequences by hybridization. Primers and probes of use in the invention may have identical or different sequences.

A "strain" is a subset of a bacterial species differing from other bacteria of the same species by an identifiable difference.

As used herein, the term "nucleic acid" is used interchangeably with the term "polynucleotide", "polynucleotide sequence" and "polynucleotide molecule". In addition, all of these listed terms may refer to a portion of a gene or to an entire gene, and the term "gene" is used interchangeably herein as the term "polynucleotide", "polynucleotide sequence", "polynucleotide molecule" and "nucleic acid".

A "mecA polynucleotide sequence" refers to a polynucleotide that comprises a sequence encoding a portion or all of a mecA gene.

Overview

The present invention provides methods for detecting and analyzing antibiotic-resistant bacteria. Although the invention is described herein primarily with respect to bacteria resistant to the antibiotic methicillin, it will be appreciated that the methods and compositions of the present invention can be used to detect bacteria resistant to a wide range of antibiotics, including in one non-limiting example, vancomycin. The flexibility of the assays and compositions encompassed by the present invention is due in part to the flexibility in the ability of bacteria to acquire genes that provide antibiotic resistance. The acquisition of such genes is often facilitated by plasmids, transposons, integrons and archetype insertion elements. Because bacteria acquire antibiotic resistance in known ways, it will be appreciated that the methods and compositions of the present invention can be adapted using methods known in the art to detect different types and strains of bacteria that are resistant to various antibiotics. Information on acquisition of antibiotic resistance can be found, for example, in Toleman, et al., (2006), *Journal of Antimicrobial Chemotherapy* 58:1-6; Handwerger et al., (1995), *Antimicrobial Agents And Chemotherapy*, pp. 2446-2453; Launay, et al., (2006), *Antimicrobial Agents And Chemotherapy*, pp. 1054-1062, all of which are hereby incorporated by reference in their entirety for all purposes and in particular for their teachings regarding the acquisition of antibiotic resistance in bacteria.

In one aspect, the invention provides a cycle threshold assay for detecting the presence of methicillin-resistant bacteria in a sample. In a further aspect, such an assay can also be used to determine whether a detected methicillin-resistant bacteria is *Staphylococcus aureus* ("*S. aureus*"). In addition, the present invention provides methods and assays for distinguishing between different strains of *S. aureus*, and for determining whether the strain present in a sample is an emerging strain not previously identified and/or sequenced.

In one aspect, the cycle threshold assay of the invention utilizes amplification reactions directed to three different loci in a bacterial genome. In one exemplary aspect, for detection of MRSA, these three different loci are (i) the mecA gene, (ii) a bridging region between the SCCmec insertion cassette and the orfX gene, and (iii) an *S. aureus*-specific gene that is not orfX. In another exemplary embodiment, a region of a methicillin-susceptible *S. aureus* (MSSA) is amplified—this region is the region of the orfX gene surrounding the position at which an insertion cassette would be inserted but does not have that insertion cassette (this region is also referred to herein as "MSSA-orfX"). In these exemplary embodiments, the cycle at which amplification products for each locus appears indicates whether MRSA is present in the sample. As used herein, the cycle at which an amplification product "appears" refers generally to the cycle at which the amplification product is detectable—in exemplary embodiment, the product "appears" at the first cycle number at which the amplification product has accumulated to enough of a concentration to be detected using methods known in the art and described further herein. In a further embodiment, the cycle number can also provide information as to the strain of MRSA that is present, and whether any other non-*Staphylococcus* mec-resistant bacteria are present in the sample.

Methods of the invention can be used to detect bacteria from samples obtained from a variety of sources, including without limitation: clinical samples (e.g. a body fluid such as nasal fluids, whole blood, serum, plasma, cerebrospinal fluid, urine, lymph fluids, and various external secretions of the respiratory, intestinal and genitourinary tracts, tears, saliva, milk as well as white blood cells, malignant tissues, amniotic fluid and chorionic villi), environmental samples, microbial cultures, microbial colonies, tissues, and cell cultures. Samples may also be obtained from food, from surfaces (such as floors, tables, and the like), and from airborne particles (including without limitation pollen and dust). Samples of used in the present invention may be pure samples or impure samples. Samples for use in the invention may comprise a mixture from two or more distinct strains of bacteria.

In one embodiment, once a sample is obtained, polynucleotide sequences may be directly assayed from the sample. In another embodiment, polynucleotides, such as DNA, are first extracted from the sample using methods known in the art and then used in the assays of the invention.

Cycle Threshold Assay

The invention provides methods for detecting and analyzing antibiotic-resistant bacteria using a cycle threshold assay. In general, a cycle threshold assay of the invention utilizes a multi-cycle amplification reaction in which the cycle at which a particular amplification product appears relative to other co-amplified fragments can provide information on the strains and species of bacteria present in the sample. In addition, the cycle threshold assay can provide information on the presence of a specific antibiotic-resistant strain, such as, but not limited to, bacterial strains resistant to methicillin. Although the cycle threshold assay of the invention is primarily described herein in terms of real-time PCR, it will be appreciated that other template-based amplification reactions can be adapted for use in accordance with the present invention using methods known in the art and described further herein.

The term "detecting and analyzing" encompasses confirming the presence of a particular species or strain of bacteria as well as distinguishing between different species and strains of bacteria. The term also encompasses determining the concentration or relative concentrations of different species or strains of bacteria in a sample.

In one aspect, an amplification reaction is provided such that nucleotide fragments from at least three different loci of a bacterial genome are amplified. By determining the cycle number at which fragments from each locus appears, it is possible to differentiate between a sample containing a single bacterial species (a single strain) and a sample containing a mixture of different bacterial species and/or strains. Generally, if a sample contains a mixture of different strains or species of bacteria, and if the different strains or species have at least a 10-times factor difference in their relative concentrations, amplification products from loci which are found in more than one species or strain of bacteria will appear at a cycle number significantly removed (by 4 cycles or more) from the amplification products from loci which are found in only a single species or strain of bacteria. However, if only a single species or strain is present in the sample, (or if there is a mixture of strains or species which have less than a 10-times factor difference in their concentrations) the amplification products from all loci will appear at substantially the same (within 3 cycles) point of a multi-cycle amplification cycle.

Cycle Threshold Assay: MRSA

In one aspect, cycle threshold assays of the invention are used to detect and analyze MRSA in a sample. As used herein, the term "MRSA" refers to any strain or sub-strain of *Staphylococcus aureus* bacteria which is resistant to the effects of the antibiotic methicillin by virtue of acquiring a *staphylococcal* cassette chromosome mec (SCCmec) element containing a functional mecA gene. An exemplary MRSA DNA sequence is set forth in Genebank Accession No. NC_002745.

It has been shown that methicillin-susceptible *S. aureus* (MSSA) strains become MRSA strains by the acquisition of a *Staphylococcal* cassette insertion (SCCmec) element carrying the mecA gene. This cassette is generally (but not exclusively) obtained from other *Staphylococci* and non-*Staphylococci* bacteria. The mecA gene provides the methicillin resistance characteristic of certain *S. aureus* strains. The mecA gene encodes a β-lactam-resistant penicillin-binding protein (PBP), which takes over the biosynthetic functions of the normal PBPs when the cell is exposed to β lactam antibiotics.

In one exemplary embodiment, the invention may provide methods and compositions for the amplification of polynucleotide sequences (also referred to herein as "fragments") from: (i) the mecA gene locus, (ii) a locus for an *S. aureus* specific gene, and (iii) the locus for the "bridging region" between the 3' end of the SCCmec region and the orfX gene. In this embodiment, if the sample contains an MRSA strain that cannot be detected by any of the primers for the bridging region (i.e., is a newly emerging strain that has not been identified and/or sequenced previously), then the mecA amplification product and the *S. aureus* specific amplification product will appear at identical or substantially identical cycle numbers (e.g., no more than 3 cycles apart in either direction).

If the mecA fragment and the *S. aureus* specific gene fragment appear at substantially different cycle numbers (e.g., 4 or more cycles apart in either direction), this indicates that the sample is a mixed bacterial sample comprising both *S. aureus* and another methicillin-resistant bacteria with at least a 10-times factor difference in their concentrations. This difference in cycle number appearance is generally a result of the mecA fragment being amplified from both populations of bacteria, whereas the *S. aureus*-specific gene fragment would be amplified only from the *S. aureus* bacteria.

In another exemplary embodiment, a cycle threshold assay of the invention amplifies provides methods and compositions for the amplification of fragments from: (i) the mecA gene locus, (ii) a locus for an *S. aureus* specific gene, and (iii) the orfX region surrounding the SCCmec insertion site for an MSSA bacteria that does not contain the SCCmec element (referred to herein as the "MSSA-orfX region"). In this embodiment, if the *S. aureus*-specific fragment appears 4 or more cycles sooner than the MSSA orfX region fragment, this is an indication that the sample comprises a mixture of both MSSA and MRSA bacteria with at least a 10-times factor difference in their concentrations. The reasoning is that the orfX gene fragment will reflect amplified sequence from only MSSA bacteria, while the *S. aureus*-specific fragment will reflect the combined amplified sequence from MSSA and MRSA bacteria.

In another embodiment, if the *S. aureus*-specific fragment appears at substantially the same cycle (i.e., no more than 3 cycles apart in either direction) as the MSSA-orfX gene fragment, this will indicate that the sample does not comprise MRSA and instead contains a mixture of MSSA bacteria and non-*Staphylococcus* mec-resistant bacteria. This is because both the MSSA-orfX amplification product and the *S. aureus*-specific amplification product would be derived only from the MSSA in the sample. In addition, if the concentration of mec-resistant bacteria in the sample is at least 10 times different than the concentration of MSSA bacteria in the sample, mecA will appear at a cycle number at least 4 cycles separate from the MSSA-orfX and *S. aureus*-specific fragments, because mecA would be amplified from a separate population from the MSSA-orfX and *S. aureus*-specific fragments.

In the unusual case that MSSA and non-*S. aureus* methicillin resistant bacteria are present in the sample in similar concentrations, then the MSSA-orfX and *S. aureus*-specific fragment will both reflect amplified sequence derived only from the MSSA and should appear at substantially identical cycle numbers (e.g. no more than 3 cycles apart) from each other. In addition, as the mecA fragment will reflect amplified sequence derived only from the non-*S. aureus* methicillin-resistant bacteria in similar concentration, it should also appear at a cycle number substantially identical to the other two fragments (e.g. no more than 3 cycles apart).

In accordance with the invention, cycle number analysis may be performed manually or the analysis may be performed using instruments and software engineered for performing such a task. Manual and automated methods of performing cycle number analyses of the invention are known in the art and described further herein.

In one embodiment, all of the amplification reactions in the cycle threshold assay are performed in the same aliquot of the sample. In another embodiment, one or more of the amplification reactions will be performed in different aliquots of the sample.

The following describes in greater detail the specifics of the primers that can be used in cycle threshold assays as well as other assays described herein for detecting antibiotic-resistant bacteria.

Primers Directed to mecA

In one aspect, primers directed to the mecA region of the *Staphylococcus* genome are provided for cycle threshold assays of the invention. As used herein, primers "directed to" a particular region or polynucleotide sequence refers generally to primers that are capable of amplifying a particular region or polynucleotide sequence. In one embodiment, such primers are able to hybridize with and/or anneal to a particular genomic region or polynucleotide sequence. These primers may be perfectly complementary to the particular genomic region or polynucleotide sequence, or they may have lesser complementarity but are nevertheless still able to anneal/hybridize to the appropriate region and serve as a starting point for amplification reactions. Primers of the invention may also be used as probes in hybridization reactions.

In one embodiment, mecA primers of the invention can hybridize to a mecA gene as set forth in GenBank accession no. X52593. In a further embodiment, mecA primers of the invention have sequences as set forth in SEQ ID NOs: 10-11.

In one embodiment, primers directed to the mecA region used in accordance with the invention have 100% sequence identity to SEQ ID NOs: 10-11. In a further embodiment, the primers have about 70%, 75%, 80%, 85%, 90%, 95%, 97%, 98%, and 99% sequence identity to SEQ ID NOs: 10-11.

Primers Directed to the Bridging Region between SCCmec and orfX

In one aspect, methods of the invention utilize primers directed to the bridging region between the 3' end of the SCCmec and the adjacent junction region of the orfX gene.

It will be appreciated that a high degree of polymorphism exists both at the 3' end of the SCCmec and at the adjacent junction region the orfX gene, which accounts for the differentiation of at least 39 different strains of MRSA. For example, the Type III strain of MRSA has a unique nucleotide sequence in the SCCmec, while type II has an insertion of 102 nucleotides to the right terminus of SCCmec, as described with additional detail by Huletsky et al (U.S. Pat. Appl. No. 20050019893). Sequence information pertaining to different strains of MRSA may be found in: Ito et al., (2001), *Antimicrob. Agents Chemother.* 45:1323-1336; Hiramatsu et al., (1996), *J. Infect. Chemother.* 2:117-129 and Ma et al., (2002), *Antimicrob. Agents Chemother.* 46:1147-1152 and Huletsky et al (U.S. Pat. Appl. No. 20050019893), all of which are hereby incorporated by reference in their entirety for all purposes and in particular for their teachings regarding sequences for different strains of MRSA.

Thus, the present invention contemplates the use of a battery of primers (also referred to herein, as bridging primers) that are capable of detecting the bridging region in different strains of MRSA, including the most promiscuous strains (types I-IV) and newly emerging strains.

Exemplary primers directed to bridging regions are set forth by SEQ ID NOs: 2-8. In one embodiment, at least 2 bridging primers are used in assays of the present invention. In a further embodiment, at least 5 bridging primers are used in assays of the present invention. In still further embodiments, about 3 to about 30, about 5 to about 25, about 7 to about 20, about 9 to about 15 and about 10 to about 12 bridging primers are used in accordance with the present invention.

In one embodiment, primers directed to the bridging region have 100% sequence identity to SEQ ID NOs: 2-8. In a further embodiment, the primers have about 70%, 75%, 80%, 85%, 90%, 95%, 97%, 98%, and 99% sequence identity to SEQ ID NOs: 2-8.

Primers Directed to MSSA-orfX

As described herein, in one aspect, the invention provides assays in which locus is amplified using a primer set directed to the orfX region surrounding the SCCmec insertion site as would uniquely be found in a MSSA bacteria not containing the SCCmec element. This region is also referred to herein as "MSSA-orfX". Exemplary primers capable of amplifying a DNA fragment comprising the MSSA-orfX are set forth by SEQ ID NOs: 2 and 24.

Primers Directed to an *S. aureus* Specific Locus

A primary weakness of traditional detection methods for rapidly evolving bacteria, such as MRSA, is that amplification of one or two loci can result in false negatives, particularly when a sample contains a newly emerging strain of the target bacteria. In one exemplary aspect, the present invention provides methods and compositions for avoiding such false negatives through amplification of three different loci, including an *S. aureus*-specific locus. In one embodiment, the *S. aureus*-specific locus is not within the orfX or bridging region of the bacterial genome. Examples of *S. aureus*-specific genes include, but are not limited to: nuc, Sa442 and femB. Exemplary primers capable of amplifying a DNA fragment comprising a nuc polynucleotide sequence are set forth by SEQ ID NOs: 18 and 19. Exemplary primers capable of amplifying a DNA fragment comprising a Sa442 polynucleotide sequence are set forth by SEQ ID NOs: 13 and 14.

In one aspect, amplification of a third *S. aureus*-specific locus allows the use of fewer primers directed to the bridging region between SCCmec and orfX (e.g. primers of SEQ ID NOs: 2-8) while still retaining the accuracy of the cycle threshold assay in detecting not only the most promiscuous strains of MRSA, but also other strains of MRSA, including newly emerging strains. Achieving such a high degree of accuracy using bridging primers alone could entail the use of a vast number of additional bridging primers, which could in turn reduce the effectiveness and efficiency of a multiplex PCR reaction.

Primers Used as an Internal Control

It will be appreciated that assays of the present invention may also include an internal control to confirm the competence of the PCR reaction components (i.e. DNA polymerase, deoxynucleotides etc.) and to confirm that the DNA extraction procedure does not contain any PCR inhibitors which could result in a false negative. Thus, the present invention provides assays which include amplification of polynucleotide sequences unrelated to the target regions of the bacterial genome. For example, human polynucleotide sequences, such as those related to housekeeping genes or a well-characterized gene such as β-globin may be used as internal controls in assays of the invention. Exemplary primers that may be used as such internal controls are set forth by SEQ ID NOs: 16 and 17.

In one embodiment, amplification reactions for such internal control loci are conducted in the same aliquot of the sample as other amplification reactions for the cycle threshold assay of the invention. In another embodiment, the internal control amplification reaction is conducted in a different aliquot of the sample than the other amplification reactions for the cycle threshold assay.

Cycle Threshold Assay: Vancomycin

As described above for detection and analysis of bacteria resistant to methicillin, the present invention encompasses similar methods and compositions for the detection and analysis of bacteria resistant to other antibiotics, including vancomycin.

As is the case for many types of antibiotic-resistance, vancomycin-resistance is conferred by insertion into the bacterial genome of an element containing a functional van gene. Cycle threshold assays of the invention can be used to detect and analyze bacteria that are vancomycin resistant through detection of a region of the bacterial genome containing at least a portion of a van gene. In one exemplary embodiment, a cycle threshold assay of the invention will utilize primers capable of amplifying the van gene region. Such primers are designed according to methods described herein and known in the art. In one exemplary embodiment, such primers may by complementary to a portion of the van gene. In another exemplary embodiment, such primers may be complementary to polynucleotide sequences outside of the van gene region but that are nevertheless capable of amplifying the van gene region. The van gene region is known in the art, and vancomycin-resistance is conferred by a number of genes, including for example vanA, vanB1, and van B2.

In a further embodiment, cycle threshold assays of the invention will utilize primers capable of amplifying van as well as two other loci in the bacterial genome. The other two loci amplified in such an embodiment may include bridging regions between the van region and the insertion point and regions of the bacterial genome that are species and/or strain-specific. For exemplary bridging region polynucleotide sequences, see Launay et al., (2006) *Antimicrob. Agents and Chemother.* 50(3): 1054-62, which is hereby incorporated by reference in its entirety for all purposes and in particular for its disclosure of target polynucleotide sequences in vancomycin resistant bacterial strains, some of which are listed in FIG. 1 as SEQ ID NOs: 25-38. Primers complementary to sequences such as those listed in FIG. 1 may be used in cycle threshold assays and triple locus assays of the invention, as disclosed herein. In some embodiments, such primers have 100% sequence identity to the sequences listed in FIG. 1 (SEQ ID NOs: 25-38). In a further embodiment, the primers have about 70%, 75%, 80%, 85%, 90%, 95%, 97%, 98%, and 99% sequence identity to SEQ ID NOs: 25-38.

Another locus that can be amplified according to methods of the invention is a locus for a gene that is specific for a particular species or strain of bacteria that has acquired vancomycin resistance. For example, vancomycin resistance has been detected in strains of *Staphylococcus aureus, Oerskovia turbata, Aracanobacterium haemolyticum, Streptococcus bovis, Streptococcus gallolyticus, Streptococcus lutetiensis, Bacillus circulans, Paenibacillus, Rhodococcus, Enterococcus*, as well as anaerobic bacteria belonging to the *Clostridium* genus and *Eggerthella lenta*. Cycle threshold assays of the invention may include primers capable of amplifying genes and loci that are specific to these strains. Thus, primers directed to strain-specific loci, together with primers directed to the bridging region and a van gene region, a cycle threshold assay as described herein can be used to detect the presence of vancomycin resistant bacteria in a sample and to identify the species and/or strain of the vancomycin-resistant bacteria in the sample.

Triple Locus Assay

A triple locus assay of the invention utilizes amplification reactions similar to those described herein for the cycle threshold assay. In a triple locus assay of the invention, primers directed to three different loci are used in amplification reactions to determine which of the three loci are present in a sample. The combination of loci detected provides information on whether an antibiotic-resistant bacterial strain is present in the sample. In a further embodiment, the combination of loci detected also provides information on whether different strains and/or species of bacteria are present within a sample.

In one aspect, the triple locus assay of the invention amplifies: (i) a region comprising a gene that confers antibiotic-resistance; (ii) a "bridging region" between a gene that confers antibiotic resistance and the point in the genome at which an element containing that gene is generally inserted; and (iii) a region comprising a strain-specific gene.

In one exemplary aspect, the invention provides a triple locus assay that can be used to distinguish between MRSA and other mecA gene carrying bacteria in a sample. The triple-locus assay of the present invention provides an advantage over traditionally used methods of detecting MRSA in a sample, because the triple locus assay of the invention has a lower possibility of producing a false-negative or false-positive result. In addition, the assay of the invention is able to identify novel emerging strains of MRSA and distinguish these strains from other Staphylococcus species.

In one aspect, the triple locus assay of the invention includes methods and compositions by which three different loci of the bacterial genome are amplified: (1) at least a portion of the mecA region; (2) at least a portion of the orfX sequence; and (3) at least a portion of an S. aureus specific gene that is not orfX. In one embodiment, polynucleotide sequences from these loci are amplified utilizing primers such as those described herein which are directed to those regions of the bacterial genome. In another embodiment, one or more of the amplification products for the three loci are detected using probes that are able to hybridize to those regions. Such probes may have the same or different sequences as the primers used in the amplification reactions, and can be used to detect the presence of these loci using methods well established in the art.

In one aspect, the combination of the three loci detected in a triple locus assay of the invention provides information as to whether MRSA is present in the sample, whether other, non-S. aureus mecA-carrying bacteria are present in the sample, and whether MSSA is present in the sample. In a further aspect, the triple locus assay will identify whether the strain(s) of MRSA present in a sample are novel, emerging strains.

According to one exemplary aspect of the present invention, of the three loci interrogated in the assay, two DNA sequences, (the first comprising a mecA polynucleotide sequence and the second comprising the bridging region) are amplified. Detection of both sequences indicates that the Staphylococcus aureus bacteria present in the sample comprise a Staphylococcus aureus bacteria with SCCmec and a mecA gene and are most likely resistant to methicillin. Detection of only the mecA sequence indicates that the sample comprises one or more strains of non-Staphylococcus aureus bacteria that carry the mecA gene and are most likely methicillin-resistant. Detection of only the bridging sequence indicates that there are Staphylococcus aureus bacteria in the sample which do not comprise an MRSA-type SCCmec which includes the mecA gene (i.e. MSSA). Table 1 below provides a summary of some of the possible outcomes of a triple locus assay according to this aspect of the present invention:

TABLE 1

| | MecA (fragment 1) | Bridging region (fragment 2) | S. aureus-specific gene (fragment 3) | Result |
|---|---|---|---|---|
| A | Yes | Yes | Yes | Sample contains MRSA and may also contain one or more bacteria carrying the mecA gene |
| B | Yes | No | Yes | Sample may comprise a strain of MRSA undetectable by bridging region primers or sample may comprise a mixture of MSSA and a second non-S. aureus bacteria that is methicillin-resistant |
| C | No | Yes or No | Yes or No | Sample does not contain MRSA, but may contain an atypical strain of MSSA (if both fragment 2 and fragment 3 are present) |
| D | Yes | No | No | Sample does not contain MRSA but does contain methicillin-resistant non-S. aureus bacteria. |

As can be seen from Table 1, in the event of outcome "A", "C" or "D", a clear-cut result is obtained and no further analysis is required—in the event of outcome "A" it can be deduced that the sample comprises MRSA. In the event of outcome "C" or "D", it can be deduced that the sample most likely does not comprise MRSA. However, in the event of outcome B, no deduction can be made with any degree of certainty. In the case of such an ambiguous outcome, a cycle threshold assay as described herein can be used to further identify the bacteria present in the sample.

In another exemplary aspect, the invention provides methods and compositions for amplifying the following loci: a mecA polynucleotide sequence, an S. aureus-specific polynucleotide sequence that is not the orfX gene (also referred to herein as "SA"), and an orfX polynucleotide sequence of the orfX gene surrounding the integration site of the SCCmec as would be found in a methicillin-sensitive S. aureus bacteria that does not contain an SCCmec element (also referred to herein as "MSSA-orfX"). Detection of the first two sequences together with non-detection of the third sequence indicates that the sample contains Staphylococcus aureus bacteria resistant to methicillin (i.e. MRSA). Detection of the SA specific sequence and the MSSA-orfX sequence together with non-detection of the mecA sequence indicates that the sample comprises *Staphylococcus aureus* bacteria that are not methicillin-resistant (i.e. MSSA). Detection of mecA and the MSSA-orfX sequences and the absence of the SA sequence indicate that the sample contains a mutated MSSA and also contains methicillin-resistant bacteria other than *S. aureus*. Detection of amplification products from a single one of the regions and the absence of amplification products from the other two regions indicates that the sample does not contain MRSA.

The amplification reactions for each locus in the triple locus assay of the present invention may be conducted in the same tube (i.e. using a single aliquot of the sample) or two or more separate tubes (i.e. using a second and or third aliquot of the sample). In one exemplary embodiment, the amplification of all three sequences is conducted simultaneously in the same tube (i.e. as a multiplex reaction).

Table 2 below provides a summary of some of the possible outcomes of the assay according to this aspect of the present invention:

TABLE 2

| | MecA (fragment 1) | SA (fragment 2) | MSSA-orfX (fragment 3) | Result |
|---|---|---|---|---|
| A | Yes | Yes | No | Sample contains MRSA |
| B | No | Yes | Yes | Sample does not contain MRSA but does contain MSSA |
| C | Yes | No | Yes | Sample does not contain MRSA but does contain methicillin-resistant non-*S. aureus* bacteria and an atypical strain of MSSA |
| D | Yes | No | No | Sample does not contain MRSA but does contain methicillin-resistant non-*S. aureus* bacteria |
| E | No | No | No | Sample does not contain MRSA or any *Staphylococcus* or other methicillin-resistant bacteria |
| F | No | Yes | No | Sample does not contain MRSA but does contain an atypical strain of MSSA |
| G | No | No | Yes | Sample does not contain MRSA but does contain an atypical strain of MSSA |
| H | Yes | Yes | Yes | Sample contains MSSA and also contains one or more bacteria carrying the mecA gene, possibly MRSA, or a methicillin-resistant non-*S. aureus* bacteria |

As can be seen from Table 2, in the event of outcome "A", "B", "C", "D", "E", "F" or "G" a clear-cut result is obtained and no further analysis is required—in the event of outcome "A" it can be deduced that the sample comprises MRSA. In the event of outcome "B", "C" "D", "E", "F" or "G", it can be deduced that the sample most likely does not comprise MRSA. However, in the event of outcome H, a mixed sample is evident that contains MSSA and one or more bacterial strains carrying the mecA gene, but it is unclear if the methicillin-resistant bacteria reflect MRSA, a non-*S. aureus* bacteria, or both. In the case of an ambiguous result such as outcome H, a cycle threshold assay of the invention can be used to identify bacteria present in the sample.

In one embodiment, triple locus assays of the invention can be used to distinguish between different strains of bacteria in a sample. As shown in FIG. 2, MRSA and MSSA bacteria can be distinguished based on detection of the products of amplification reactions directed to the bridging region, the mecA gene region, an *S. aureus*-specific polynucleotide sequence (in this embodiment, the nuc gene), and a human beta globin polynucleotide sequence (used as an internal control). In the MRSA samples, all four amplification products were detected. In contrast, in the MSSA samples, only the *S. aureus*-specific and the internal control human beta globin polynucleotide were detected.

Figure 3:
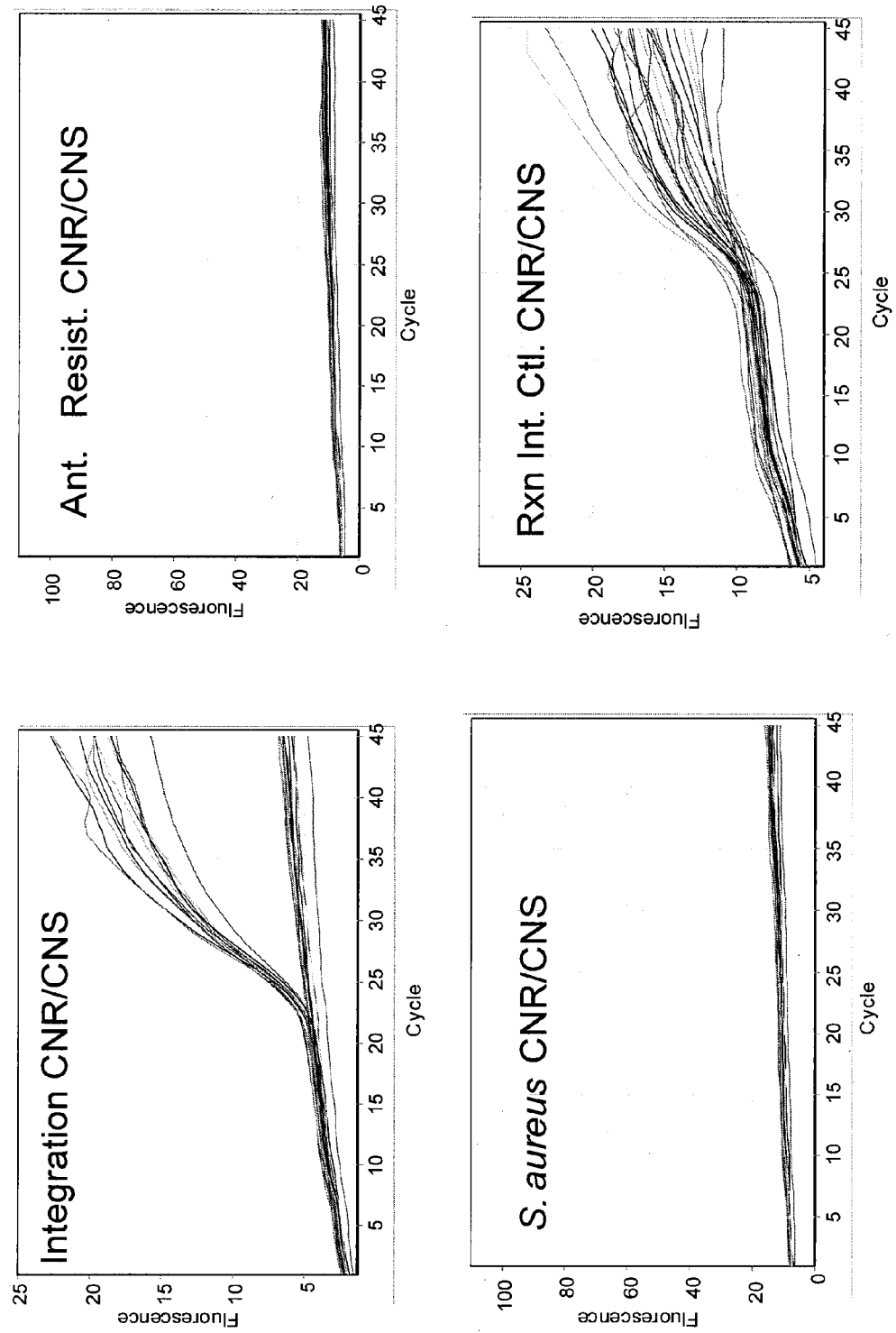
FIG. 3 illustrates results for detection of and discrimination between coagulase negative *Staphylococcus* methicillin resistant (MR-CoNS) and coagulase negative *Staphylococcus* methicillin sensitive (MS-CoNS) bacteria.

Similarly, FIG. 3 shows the results of assays which distinguish between coagulase negative *Staphylococcus* methicillin resistant (MR-CoNS) and coagulase negative *Staphylococcus* methicillin sensitive (MS-CoNS) bacteria. Again, in these experiments, the amplification reactions were directed to the bridging region, the mecA gene region, an *S. aureus*-specific polynucleotide sequence (in this embodiment, the nuc gene), and a human beta globin polynucleotide sequence (used as an internal control). In this case, for the samples containing MR-CoNS, the mecA gene polynucleotide sequence and the internal control polynucleotide sequences were detected, whereas in samples containing MS-CoNS, only the internal control polynucleotide sequence was detected. Thus, the assays of the present invention provide the ability to distinguish among MRSA, MSSA, MR-CoNS and MS-CoNS bacteria.

Advantages of the Triple-Locus Assay

As discussed herein, triple locus assays of the invention are more accurate than traditional methods of detecting antibiotic-resistant bacteria. In particular, triple locus assays result in significantly fewer false positive and negative results than double or single locus assays.

Double locus assays, (see e.g., Reischl et al., J. Clin. Microbiol. 38:2429-2433), which are generally based on the detection of the mecA gene and *S. aureus*-specific chromosomal sequences often encounter difficulty in discriminating MRSA from methicillin-resistant coagulase-negative *staphylococci* (MR-CoNS), because the mecA gene is widely distributed in both *S. aureus* and CoNS species. As more than 90% of nasal swabs contain *staphylococci*, (usually coagulase-negative *staphylococci*), and as 70-80% of CoNS are MR-CoNS (Becker et al, (2006), *J. Clin. Microbiol.* 44:229-231; Diekema et al, (2001), *Clin. Infect. Dis.* 32(Suppl. 2):S114-S132), many mixed population samples containing MSSA and MR-CoNS may be mistakenly identified as MRSA. Consequently, double locus assays are characterized by a high percentage of false positive MRSA with a low positive predictive value (PPV), and usually cannot be applied on specimens potentially containing a mixed bacterial population.

Single-locus assays have been suggested to overcome the above-described difficulties in the double locus assays.

Single locus assays are generally based on the detection of the right extremity of the SCCmec element inserted adjacent to the *S. aureus*-specific orfX gene (see e.g., Huletsky et al, (2004), *J. Clin. Microbiol.* 42:1875-1884). However, new strains of MRSA are constantly emerging with mutations on both sides of this junction (Hansse et al., (2004), *Antimicrobial Agents Chemotherapy,* 48:285-96; Sundsfjord et al., (2004), *APMIS,* 112:815-8137; Witte et al., (2005), *Eur J Microbiology and Infectious Diseases,* 24:1-5). As such, single locus assays for MRSA are characterized by false negatives. Furthermore, the single-locus assay cannot differentiate between a SCCmec element comprising the mecA gene and an SCCmec which does not carry the mecA gene.

Hiramatsu et al (U.S. Pat. No. 6,156,507) describe a single locus assay designed to detect amplification of the orfX gene surrounding the integration site of the SCCmec in the absence of SCCmec insertion. In the Hiramatsu et al. assay, a negative finding is interpreted as indicative of the presence of MRSA. An assay based on a negative result is an inadequate method of determining the presence of MRSA, as a negative finding could also be obtained from a patient sample containing neither MSSA nor MRSA. Furthermore, as Hiramatsu et al point out, a patient's sample containing a mixture of MRSA and MSSA would give a positive result in these tests and be falsely interpreted as being free of MRSA. In addition, studies have shown that Hiramatsu's single locus assay lacks in clinical adequacy due to its failure to correctly detect MRSA from clinical samples reflecting MRSA strains containing SCCmec types other than I-V (see e.g., Hansse et al., (2004), *Antimicrobial Agents Chemotherapy,* 48:285-96; Sundsfjord et al., (2005) *APMIS,* 112:815-8137, 2004; Witte et al., (2005) *Eur J Microbiology and Infectious Diseases,* 24:1-5).

Another weakness of a single-locus assay is that such an assay cannot differentiate between bacteria comprising an SCCmec element which carries the mecA gene (MRSA) or an SCC element that does not carry the mecA gene (such as SCCcap present in several MSSA strains), which can thus result in a false positive. Therefore, a single locus assay of samples comprising an MSSA which carries an SCC element that does not comprise a mecA gene can result in a false positive. The potential for false positive findings undermine the clinical utility of the single-locus assay as a reliable method of screening patients as part of an infection control program. Indeed, numerous studies utilizing the single-locus assay report clinical examples of MSSA presenting false positive as pseudo-MRSA (Rupp, et al., J Clinical Microbiology, 2006, 44:2317; Deplano et al., J Antimicrobial Chemotherapy 2000, 46: 617-620; Corkill, et al. J Antimicrobial Chemotherapy 2004, 54:229-231, Lina et al. 1999, Clini. Infect. Dis. 29:1128-1132; Warren et al. J. Clin. Microbiol. 42:5578-5581).

Methods of the present invention, including both the triple-locus assay and the cycle threshold assay, show an increased accuracy over traditional methods of detecting antibiotic-resistant bacteria such as MRSA. As illustrated in Example 3, the triple locus assay of the present invention was shown to be 99.6% sensitive and 97.4% specific, displaying a degree of accuracy far greater than either the single or double locus assays described hereinabove and further in Examples 1 and 2.

Methods of Amplification and Detection

Both the cycle threshold and triple locus assays of the invention include amplification reactions that utilize primers capable of amplifying selected regions of a genome. The term "capable of amplifying" describes primers that are able to produce an amplification product that includes a selected region of the bacterial genome. Primers capable of amplifying a selected region include primers that are complementary to a sequence within the target region. Primer capable of amplifying a selected region also include primers that are complementary to regions that overlap at least a portion of the target region, as well as primers that are complementary to regions outside of a target region but that are nevertheless able to produce an amplification product that includes the target region. It will be appreciated that such primers can be designed using methods well-established in the art.

Amplification methods used in the assays of the present invention encompass any method capable of amplifying a targeted portion of a polynucleotide sequence. Such amplification methods include without limitation: polymerase chain reaction (PCR), nucleic acid sequence-based amplification (NASBA), self-sustained sequence replication (3SR), strand displacement amplification (SDA) and branched DNA signal amplification (bDNA).

In one embodiment, PCR is used as the amplification method in assays of the invention. PCR is an in vitro technique for the enzymatic synthesis of specific DNA sequences using two oligonucleotide primers that hybridize to complementary nucleic acid strands and flank a region that is to be amplified in a target DNA. A series of reaction steps, including (1) template denaturation, (2) primer annealing, and (3) extension of annealed primers by DNA polymerase, results in the exponential accumulation of a specific fragment whose termini are defined by the 5' ends of the primers.

The term "PCR" as used herein encompasses derivative forms of the reaction, including but not limited to real-time PCR, quantitative PCR, multiplexed PCR, reverse transcription PCR and the like. Reaction volumes can range from about 100 nanoliters (nl) to about 500 microliters (µl), from about 200 nl to about 250 µl, from about 500 nl to about 200 µl, from about 1 µl to about 100 µl, from about 10 µl to about 80 µl, from about 20 µl to about 60 µl, from about 5 to about 30 µl, from about 10 to about 25 µl, and from about 30 µl to about 40 µl.

"Real-time PCR" refers to a PCR method in which the amount of reaction product, i.e. amplicon, is monitored as the reaction proceeds. There are many forms of real-time PCR, which differ mainly in the detection chemistries used for monitoring the reaction product, e.g. Gelfand et al, U.S. Pat. No. 5,210,015 ("TaqMan®"); Wittwer et al, U.S. Pat. Nos. 6,174,670 and 6,569,627 (intercalating dyes, such as SYBER® Green); Tyagi et al, U.S. Pat. No. 5,925,517 (molecular beacons); all of which are incorporated herein by reference in their entirety for all purposes and in particular for their teachings regarding real-time PCR. Other exemplary detection chemistries include, but are not limited to Scorpion Primers, Sunrise Primers, and Eclipse Probes. Detection chemistries for real-time PCR are reviewed in Mackay et al, (2002) *Nucleic Acids Research,* 30:1292-1305, which is also incorporated herein by reference in its entirety for all purposes, and in particular for its disclosure of different detection chemistries for real-time PCR.

"Multiplexed PCR" refers to a PCR wherein multiple sequences are simultaneously amplified in the same reaction mixture (multi-color real-time PCR). Generally in such methods, distinct sets of primers are employed for each sequence being amplified.

"Quantitative PCR" refers to a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$ microglobulin, ribosomal RNA, and the like. Techniques for quantitative PCR are well-known to those of ordinary skill in the art, as exemplified in the following references that are incorporated by reference in their entirety: Freeman et al, (1999) *Biotechniques*, 26: 112-126; Becker-Andre et al, (1989) *Nucleic Acids Research*, 17: 9437-9447; Zimmerman et al., (1996) Biotechniques, 21: 268-279; Diviacco et al, (1992) *Gene*, 122: 3013-3020.

Generally amplification methods used in methods of the invention will utilize primers as starting points for the amplification of the template in each cycle of the reaction. In such reactions, primers anneal to a complementary site on the template (also referred to herein as "target") polynucleotide and then enzymes such as DNA polymerase are used to extend the primers along the sequence of the template polynucleotide. Primers typically have a length in the range of from about 5 to about 50, about 10 to about 40, about 12 to about 30, and about 20 to about 25 nucleotides. The length of the primers is typically selected such that the primers bind with optimal selectivity to a target polynucleotide sequence.

Generally, primers are used as pairs which include a 'forward' primer and a 'reverse' primer, with the amplification target of interest lying between the regions of the template polynucleotide that are complementary to those primers. The design and selection of appropriate PCR primer sets is a process that is well known to a person skilled in the art. Automated methods for selection of specific pairs of primers are also well known in the art, see e.g. U.S. Publication No. 20030068625. In one embodiment, a set of amplification primers can be selected such that the distance between the two primers (i.e. the length of the amplicon) is at least 5 base pairs. In another embodiment, the primers are selected such that the distance is about 5 to about 50, about 10 to about 40, and about 20 to about 30 base pairs. In one embodiment, amplicons resulting from real-time PCR methods are from about 50 to about 400 bp, from about 75 to about 300, from about 100 to about 200 and from about 180 to about 400 bp.

In one aspect, the products of amplification reactions are detected using labeled primers. In another aspect, such products are detected using probes directed to particular regions of the template nucleic acid. In still another aspect of the present invention, the assay is a molecular-beacon based assay. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., (1998) Nature Biotechnology. 16:49]. Exemplary probe sequences that may be used in assays of the present invention are set forth by SEQ ID NOs: 1, 9, 12, 15 and 20.

Kits

In one aspect, the invention provides kits that include components for performing the assays described herein.

In one embodiment, the invention provides kits comprising reaction mixes for use in real time amplification assays. Such reaction mixes can be stabilized mixes containing all the constituents for performing the reaction in one or more containers (such as tubes for use in a PCR machine). In an exemplary embodiment, such stabilized reaction mixes include primers, fluorescently labeled probes. In a further embodiment, such mixes are stabilized such that they can be stored at room temperature.

It will be appreciated that kits of the present invention may include primers for use in assays of the invention to detect and analyze antibiotic-resistant bacteria. In one embodiment, kits of the invention include primers of use for the identification of MRSA. A kit of the present invention may, if desired, be presented in a pack which may contain one or more units of the kit of the present invention. The pack may be accompanied by instructions for using the kit. The pack may also be accommodated by a notice associated with the container in a form prescribed by a governmental agency regulating the manufacture, use or sale of laboratory supplements, which notice is reflective of approval by the agency of the form of the compositions.

A kit of the present invention may comprise primers for amplifying a polynucleotide sequence from mecA and bridging regions, as described herein. The kit may also comprise primers for amplifying a polynucleotide sequence for an *S. aureus*-specific gene and primers for amplifying a region used as an internal control, which could encode, for example, a human gene. The kit may also comprise other components of the PCR reaction including but not limited to DNA polymerase, dNTPs, magnesium, buffers and stabilizers.

According to one embodiment, a kit of the invention will include a mixture containing the components of a PCR reaction as described above. In a further embodiment, such a mixture is dehydrated by at least 50%. The dehydrating may be effected by any means known in the art, including, but not limited to: oven heating, lyophilization, and vacuum hydration removal. According to a still further embodiment, at least one of the amplification primers and probes of the present invention are incorporated into such a PCR reaction mixture prior to dehydration.

According to yet another embodiment, the reaction components including DNA polymerase, dNTPs, magnesium and stabilizers and all the reaction primers and probes to be used in an assay of the present invention may be dehydrated by at least 50% to form a ready-to-use mix that can be stored at room temperature without degradation for at least 40 days. Such a mix may be stored in a microtube, a microtube strip, or a multi-well plate. Kits comprising such dehydrated components can be utilized by laboratory personnel with limited training and experience with reduced risk of carry-over cross contamination or experimental error. Furthermore, the kits of the present invention can be transported without a need for packing in dry-ice, enabling easier delivery.

An example of the shelf-life performance of a stabilized reaction mixture in kits of the invention is shown in FIG. 4. In these experiments, reaction mixtures stored at room temperature were assayed after 5 and 10 weeks of storage and were compared to samples stored at −20° C. FIG. 4A shows the results from RNase P gene amplification and 4B shows the results from human beta globin gene amplification. For both amplification reactions, the stabilized (room temperature storage) mixes showed similar results to the reaction mixes stored at −20° C. at both the 5 week and 10 week time points.

Embodiments and Combinations Encompassed in the Scope of the Invention

In one aspect, the invention provides a method of detecting methicillin-resistant *S. aureus* (MRSA) in a sample. In this aspect, the method includes the steps: (i) providing a first set of primers where the primers are complementary to at least a portion of a mecA polynucleotide sequence; (ii) providing a second set of primers, where the primers are complementary to at least a portion of a bridging region; (iii) providing a third set of primers, where the primers are complementary to at least a portion of an *S. aureus*-specific polynucleotide sequence, and where the *S. aureus*-specific polynucleotide sequence is not an orfX polynucleotide; (iv) combining the first, second and third set of primers with the sample in a reaction mixture; (v) performing a multi-cycle amplification reaction with the reaction mixture; and (vi) determining cycle numbers of appearance of each of the mecA, bridging region and S. aureus-specific polynucleotide sequences. In this aspect, the cycle numbers indicate whether MRSA is present in a sample.

In accordance with the above, the invention further provides a method in which the first set of primers includes a plurality of primers with sequences according to at least one of SEQ ID NOs: 10-11.

In accordance with any of the above, the invention further provides a method in which the second set of primers includes a plurality of primers with sequences according to at least one of SEQ ID NOs: 2-8.

In accordance with any of the above, the invention further provides a method in which the third set of primers includes a plurality of primers with sequences according to at least one of SEQ ID NOs: 13-14 and 18-19.

In accordance with any of the above, the invention further provides a method in which the amplification reaction is a real-time polymerase chain reaction (PCR).

In accordance with any of the above, the invention further provides a method which includes the additional steps: contacting the sample with primers complementary to at least a portion of a human gene polynucleotide sequence; amplifying the human gene polynucleotide sequence; and detecting the amplified human gene polynucleotide sequence.

In accordance with any of the above, the invention further provides a method in which the S. aureus-specific polynucleotide sequence is at least a portion of a gene, which is a member selected from nuc, Sa442, and femB.

In accordance with any of the above, the invention further provides a method in which the S. aureus-specific polynucleotide sequence is at least a portion of the gene nuc.

In accordance with any of the above, the invention further provides a method in which the S. aureus-specific polynucleotide sequence is at least a portion of the gene Sa442.

In another aspect, the invention provides a method of detecting methicillin-resistant S. aureus (MRSA) in a sample. In this aspect, the method includes the steps: (i) determining whether a mecA polynucleotide is present in the sample; (ii) determining whether a bridging region polynucleotide is present in the sample; and (iii) determining whether an S. aureus-specific polynucleotide is present in the sample. In this aspect, the S. aureus-specific polynucleotide is not an orfX polynucleotide. In this aspect, if the mecA polynucleotide, the bridging region polynucleotide, and the S. aureus-specific polynucleotide are all present in the sample, then MRSA is present in the sample.

In accordance with the above, the invention further provides a method in which determining whether the mecA polynucleotide is present in the sample includes conducting an amplification reaction on the sample. This amplification reaction utilizes a first set of primers, and a majority of the first set of primers are complementary to at least a portion of the mecA polynucleotide.

In accordance with any of the above, the first set of primers includes at least one of SEQ ID NOs: 10-11.

In accordance with any of the above, the invention further provides a method in which determining whether the orfX polynucleotide is present in the sample includes conducting an amplification reaction on the sample, wherein the amplification reaction utilizes a second set of primers, and wherein a majority of the second set of primers are complementary to at least a portion of the orfX polynucleotide.

In accordance with any of the above, the invention further provides a method in which the second set of primers includes at least one of SEQ ID NOs. 2-8.

In accordance with any of the above, the invention further provides a method in which determining whether the S. aureus-specific polynucleotide is present in the sample includes conducting an amplification reaction on the sample, wherein the amplification reaction utilizes a third set of primers, and wherein a majority of the third set of primers are complementary to at least a portion of the S. aureus-specific polynucleotide.

In accordance with any of the above, the invention further provides a method in which the third set of primers includes at least one of SEQ ID NOs. 13-14 and 18-19.

In accordance with any of the above, the invention further provides a method in which the S. aureus-specific polynucleotide is at least a portion of a gene, which is a member selected from nuc, Sa442, and femB.

In accordance with any of the above, the invention further provides a method in which the S. aureus-specific polynucleotide is nuc.

In accordance with any of the above, the invention further provides a method in which the S. aureus-specific polynucleotide is Sa442.

In accordance with any of the above, the invention further provides a method which includes the additional steps of: contacting the sample with primers complementary to at least a portion of a human gene polynucleotide sequence; amplifying the human gene polynucleotide sequence; and detecting the amplified human gene polynucleotide sequence.

In accordance with any of the above, the invention further provides a method in which the human gene polynucleotide sequence includes at least a portion of a housekeeping gene.

In accordance with any of the above, the invention further provides a method in which the human gene polynucleotide sequence includes at least a portion of a β-globin gene.

In accordance with any of the above, the invention further provides a method in which all three polynucleotide sequences are detected simultaneously.

In accordance with any of the above, the invention further provides a method in which determining whether each of the three polynucleotide sequences are present in a sample is accomplished sequentially in any order.

In accordance with any of the above, the invention further provides a method in which determining whether each of the three polynucleotide sequences are present in a sample is accomplished in an identical aliquot of the sample.

In accordance with any of the above, the invention further provides a method in which determining whether each of the three polynucleotide sequences are present in a sample is accomplished in different aliquots of the sample.

In accordance with any of the above, the invention further provides a method in which if the mecA polynucleotide is present in the sample and the S. aureus-specific polynucleotide is present in the sample but the bridging region polynucleotide is not present in the sample, then the sample includes non-Staphylococcus methicillin-resistant bacteria.

In still another aspect and in accordance with any of the above, the invention provides a method of detecting methicillin-resistant S. aureus (MRSA) in a sample. In this aspect, the method includes the steps: (i) providing a first set of primers, where the first set of primers are complementary to at least a portion of a mecA polynucleotide sequence; (ii) providing a second set of primers, where the second set of primers are complementary to at least a portion of an MSSA-orfX polynucleotide sequence; (iii) providing a third set of primers, where the third set of primers are complementary to at least a portion of an *S. aureus*-specific polynucleotide sequence, and where the *S. aureus*-specific polynucleotide sequence is not an orfX polynucleotide; (iv) combining the first, second and third set of primers with the sample in a reaction mixture; (v) performing a multi-cycle amplification reaction with the reaction mixture; and (vi) determining cycle numbers of appearance of each of the mecA, MSSA-orfX and *S. aureus*-specific polynucleotide sequences. In this aspect, the cycle numbers indicate whether MRSA is present in a sample.

In accordance with the any of above, the invention further provides a method in which if all three sets of primers produce amplification products in an amplification reaction, and the *S. aureus*-specific polynucleotide sequence appears at a cycle at least 4 cycles removed from appearance of the MSSA-orfX polynucleotide sequence, then the sample includes both MRSA and methicillin-sensitive *S. aureus* (MSSA).

In accordance with any of the above, the invention further provides a method in which if all three sets of primers produce amplification products in an amplification reaction, and the *S. aureus*-specific polynucleotide sequence appears within 3 cycles of the MSSA-orfX polynucleotide sequence, then the sample includes MSSA and a non-*S. aureus* methicillin resistant bacteria.

In still another aspect and in accordance with any of the above, the invention provides a method of identifying bacteria in a sample. This method includes the steps: (i) determining whether a mecA polynucleotide is present in the sample; (ii) determining whether an MSSA-orfX polynucleotide is present in the sample; and (iii) determining whether an *S. aureus*-specific polynucleotide is present in the sample, where the *S. aureus*-specific polynucleotide is not an orfX polynucleotide. In this aspect, the combination of (a), (b), and (c) present in the sample identifies bacteria in the sample.

In accordance with any of the above, the invention further provides a method in which if the mecA polynucleotide and the *S. aureus*-specific polynucleotide are both present in the sample and the MSSA-orfX polynucleotide is not present in the sample, then the sample includes methicillin-resistant *S. aureus* (MRSA).

In accordance with any of the above, the invention further provides a method in which if the *S. aureus*-specific polynucleotide and the MSSA-orfX are both present in the sample and the mecA polynucleotide is not present in the sample, then the sample includes methicillin-susceptible *S. aureus* (MSSA) but does not comprise MRSA.

In accordance with any of the above, the invention further provides a method in which if the mecA polynucleotide and the MSSA-orfX polynucleotide are both present in the sample and the *S. aureus*-specific polynucleotide is not present in the sample, then the sample includes a non-*S. aureus* methicillin-resistant bacteria and the sample does not comprise MRSA.

In accordance with any of the above, the invention further provides a method in which if only one of the mecA polynucleotide, the MSSA-orfX polynucleotide and the *S. aureus*-specific polynucleotide are present in the sample, then the sample does not comprise MRSA.

In accordance with any of the above, the invention further provides a method in which the sample may comprise no bacteria, bacteria from a single strain, or a mixture of bacteria from more than one strain.

In accordance with any of the above, the invention further provides a method in which the sample is a member selected from a bodily fluid, a nasal swab, and a tissue.

In accordance with any of the above, the invention further provides a method in which the determining whether a mecA polynucleotide is present in the sample, the determining whether an MSSA-orfX polynucleotide is present in the sample, and the determining whether an *S. aureus*-specific polynucleotide is present in the sample are all amplification reactions conducted in separate aliquots of the sample.

In accordance with any of the above, the invention further provides a method in which two or more of the determining whether a mecA polynucleotide is present in the sample, the determining whether an MSSA-orfX polynucleotide is present in the sample, and the determining whether an *S. aureus*-specific polynucleotide is present in the sample are amplification reactions conducted in identical aliquots of the sample.

In another aspect and in accordance with any of the above, the invention further provides a kit for identifying MRSA in a sample, and such a kit can include: a first set of primers complementary to at least a portion of a mecA polynucleotide sequence; a second set of primers complementary to at least a portion of a bridging sequence; a third set of primers complementary to at least a portion of an *S. aureus*-specific polynucleotide sequence, wherein the *S. aureus*-specific polynucleotide sequence is not a bridging sequence; and at least one member selected from: a DNA polymerase enzyme, dNTPs, magnesium and a stabilizer.

In another aspect and in accordance with any of the above, the invention further provides a kit for identifying MRSA in a sample. Such a kit includes: a first set of primers complementary to at least a portion of a mecA polynucleotide sequence; a second set of primers complementary to at least a portion of MSSA-orfX polynucleotide sequence; a third set of primers complementary to at least a portion of an *S. aureus*-specific polynucleotide sequence, wherein the *S. aureus*-specific polynucleotide sequence is not a bridging sequence; and at least one member selected from: a DNA polymerase enzyme, dNTPs, magnesium and a stabilizer.

In one aspect and in accordance with any of the above, the invention further provides method of detecting an antibiotic-resistant bacterial strain in a sample. This method can include the steps: (i) providing a first set of primers, which are capable of producing a first amplification product from at least a portion of a gene that confers antibiotic-resistance; (ii) providing a second set of primers, which are capable of producing a second amplification product from at least a portion of a bridging region; (iii) providing a third set of primers, which are capable of producing a third amplification product from at least a portion of a bacterial strain-specific polynucleotide sequence; (iv) combining the first, second and third set of primers with the sample in a reaction mixture; (v) performing a multi-cycle amplification reaction with the reaction mixture; and (vi) determining cycle numbers of appearance of each of the first, second and third amplification products. In this aspect, the cycle numbers indicate whether an antibiotic-resistant bacterial strain is present in the sample.

In accordance with any of the above, the invention further provides a method in which the gene amplified using a first set of primers confers resistance to vancomycin.

In accordance with any of the above, the invention further provides a method in which the gene amplified using a first set of primers confers resistance to methicillin.

In accordance with any of the above, the invention further provides a method in which the bacterial strain-specific polynucleotide sequence amplified is an *S. aureus*-specific polynucleotide sequence.

A In accordance with any of the above, the invention further provides a method in which the bridging region amplified includes a polynucleotide sequence that is a member selected from SEQ ID NOs: 2-8.

The present invention may be better understood by reference to the following non-limiting Examples, which are provided as exemplary of the invention. The following examples are presented in order to more fully illustrate preferred embodiments of the invention, but should in no way be construed as limiting the broad scope of the invention.

While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in the entirety.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990), all of which are incorporated by reference as if fully set forth herein. Other general references are provided throughout this document. The procedures therein are believed to be well known in the art and are provided for the convenience of the reader. All the information contained therein is incorporated herein by reference.

Example 1

Single and Double Locus Assays Using Pure Culture Samples.

A single locus qRT-PCR assay for detecting MRSA was performed using methods based on Huletsky et al (US 20050019893 and US20060252078). This assay uses multiple primers and a dual labeled probe for hybridization of the right extremity junction of SCCmec:orfX. Detection of human β globin was added as an internal control. A dual labeled probe complementary to the *S. aureus* orfX region (SEQ ID NO: 1) was used. A forward primer complementary to the *S. aureus* orfX region (SEQ ID NO: 2) and six reverse primers complementary to MREJ sequences in the Sccmec element. "MREJ" refers to "poly-Morphic Right Extremity Junction". In Huletsky et al., US Patent Publication No. 20050019893, MREJ is a sequence toward the right end of the SCC mec cassette that is prone to mutation—many different MRSA strains will show variations in this region of their genome. Types i, ii, iii, iv and v of the SCCmec gene (SEQ ID NO: 3-SEQ ID NO: 8) were used. In place of the primers taught by Huletsky et al (2004) for hybridization to MREJ Types iv (meciv511), two slightly different primers (SEQ ID NO: 7 and SEQ ID NO: 8), each overlapping the sequence of meciv511 were used. This change provided comparable detection of MREJ Type IV, but reduced non-specific background amplification. An internal control assay was added consisting of one probe (SEQ ID NO: 15), a forward primer (SEQ ID NO: 16) and a reverse primer (SEQ ID NO: 17) in order to detect human β globin.

For the double locus assay, a qRT-PCR assay for detecting MRSA was performed as described by Reischl et al (2000), *J. Clin. Microbiol.* 38:2429-2433. This assay uses primers and probes to detect the *S. aureus* specific gene Sa442 and the mecA gene. Detection of human β globin was added as an internal control. A dual labeled probe was used with a sequence as set forth in SEQ ID NO: 12 for the detection of the *S. aureus* specific gene Sa442. A dual labeled probe was used with a sequence as set forth in SEQ ID NO: 9 for the detection of mecA. A forward primer and a reverse primer complementary to the *S. aureus* specific gene Sa442 (SEQ ID NOs: 13-14) was used. A forward primer and a reverse primer complementary to the mecA gene (SEQ ID NOs: 10-11) was used. An internal control assay was added consisting of one probe (SEQ ID NO: 15), a forward primer (SEQ ID NO: 16) and a reverse primer (SEQ ID NO: 17) in order to detect human β globin.

For both the single and double locus assays, primers as described above were added to a standard qRT-PCR reaction mixture (Absolute™ QPCR Mix from ABgene) and tested with DNA samples of known MRSA, MSSA, MS-CoNS and MR-CoNS strains. Each assay was tested on 150 pure culture samples; 50 MRSA, 50 MSSA, 25 MR-CoNS and 25 MS-CoNS. Amplification and detection reactions were run using a RotorGene 3000 System Real Time PCR instrument from Corbett Life Science according to the following standard qRT-PCR protocol:

1. 15 minute at 95° C. for enzyme activation and DNA denaturation.
2. 50 amplification cycles each consisting of the following three steps:
   Step 1—10 seconds at 95° C.
   Step 2—30 seconds at 56° C.
   Step 3—15 seconds at 72° C. (at the end of step three the readings were taken for each of the four fluorescent dyes)

The single locus assay yielded 51 SCC:orfX-positive results, of which 49 were MRSA (true positive) and 2 were MSSA (false positive). The single locus assay also yielded 99 SCC:orfX-negative results, of which one was MRSA (false negative), 48 where MSSA (true negative), 25 where MR-CoNS (true negative) and 25 where MS-CoNS (true negative). The single locus ssay resulted in a sensitivity of 98%, a specificity of 98%, a positive predictive value of 96.1% and a negative predictive value of 99% in detecting a pure culture sample.

The double locus assay yielded 50 Sa442-positive mecA-positive results, of which all 50 were MRSA (true positive). The double locus assay also yielded 48 Sa442-positive mecA-negative results, all 48 were MSSA (true negative). This assay also yielded 25 Sa442-negative mecA+ results, all 25 were MR-CoNS (true negative for MRSA). Double Locus Assay also yielded 27 Sa442-negative mecA-negative results, 25 of which were MS-CoNS (true negative) and 2 of which were MSSA (true negative for MRSA yet it is a false negative for MSSA which is suppose to contain the Sa442 gene). The double locus assay resulted in a sensitivity of 100%, a specificity of 100%, a positive predictive value of 100% and a negative predictive value of 100% in detecting a pure culture sample.

The above results demonstrate that primers used in accordance with the present invention can be successfully used to amplify target regions of the genomes for different species and strains of *Staphylococcus*.

Example 2

Demonstration of the Limited Accuracy of Single and Double Locus Assays in Differentiating MRSA from MSSA, MS-CoNS, and MR-CoNS Using Clinical Patient Samples.

qRT-PCR reactions were performed using the Single Locus Assay and Double Locus Assay as described for Example 1 herein above with 460 samples of patient DNA derived from cultured swabs which contain mixed populations. The reactions were run as described herein above utilizing a standard qRT-PCR reaction mixture (Absolute™ QPCR Mix from ABgene) and standard qRT-PCR protocol described above, with amplification and detection run using a RotorGene 3000 System Real Time PCR instrument from Corbett Life Science.

All runs contained 2 NTC samples (No Template Control), and known MRSA, MSSA, and MR-CoNS controls. Clinical samples were plated and qRT-PCR was performed the next day on *S. aureus* suspected colonies only. All samples were analyzed for mixed population using the same bacteriological needle used to sample colonies for qRT-PCR. All samples were analyzed also by conventional methods (plating on CNA, Mannitol and Chromeagar-MRSA plates (Hy-labs, Israel), visual inspection, slide agglutination (Pastorex, Bio-Rad) and plating on MH+NaCl+OXA and DNase plates (Hy-labs, Israel) for conformation.

338 samples were analyzed (after exclusion of patient duplicates (122)), 219 of which contained MRSA, of which 37% also contained other Gram-positive bacteria, 6% Gram-negative bacteria and 32% both Gram-positive and Gram-negative. Of the 119 non-MRSA samples, 8 were MS-CoNS, 16 MR-CoNS, 5 non-*staphylococcal*, and 90 MSSAs. Of the 90 MSSAs 42% contained also other Gram-positive bacteria, 2% contained Gram-negative bacteria and 21% contained both Gram-positive and Gram-negative. Of the MSSA containing samples, 49% also contained MR-CoNS. It should be noted that these percentages do not represent real percentage of nasal swabs mixed populations, but represent the mixed population sampled for qRT-PCR, biased towards Oxacyllin resistant bacteria, as many samples originated from Oxacyllin containing plates. It is expected that the proportion of such mixtures to be much higher in direct swab analysis.

All NTCs and controls were detected correctly at all runs of both assays.

The single locus assay displayed unsatisfactory accuracy with the mixed cultures. The single locus assay yielded 216 SCC:orfX-positive results, of which 203 were MRSA (true positive) and 13 where MSSA (false positive). The single locus assay also yielded 122 SCC:orfX-negative results, of which 16 were MRSA (false negative), 77 were MSSA (true negative), 16 were MR-CoNS (true negative), 8 were MS-CoNS (true negative) and 5 were non-*Staphylococcus* (true negative). The single locus assay resulted in a specificity of only 89.1% and a negative predictive value of 86.9% in detecting a mixed culture sample. The results are summarized in Table 3 herein below.

TABLE 3

| Convention Culture Identification | Single-locus Test[a] | | Double-locus Test[b] | | | |
|---|---|---|---|---|---|---|
| | SCC: orfX+ (MRSA) | SCC: orfX− (other) | Sa442+mec+ (MRSA) | Sa442+mec− (MSSA) | Sa442−mec+ (non S.A OXAr) | Sa442−mec− (other) |
| MRSA (n = 219) | 203 | 16 | 218 | 1 | — | — |
| MSSA (n = 90) | 13 | 77 | (44 + 2)[c] | 35 | — | 9 |
| MR-CoNS (n = 16) | — | 16 | — | — | 16 | — |
| MS-CoNS (n = 8) | — | 8 | — | — | — | 8 |
| Non-*Staph*. (n = 5) | — | 5 | — | — | — | 5 |

[a]sensitivity = 92.7%, specificity = 89.1%, Positive predictive value = 93.1%, Negative predicted value = 86.9%,
[b]sensitivity = 99.5%, specificity = 61.4%, Positive predictive value = 82.6%, Negative predicted value = 98.6%,
[c]44 were MSSA mixed with MR-CoNS, 2 were MRSA with non-functional mecA genes - genetically these last two were MRSA genetically, but phenotypically MSSA (also referred to herein as "mec-positive MSSA).

As summarized above in Table 2, the double locus assay also displayed unsatisfactory accuracy with the mixed cultures. The double locus assay yielded 264 Sa442-positive mecA-positive results, of which 218 were MRSA (true positive) and 46 were MSSA (false positive). Of the false negatives, 44 were determined by culture examination to be MSSA mixed with MR-CoNS and two were found to be mecA-positive MSSA, which probably originated from MRSA with mecA genes mutated to make them non-functional. Such bacteria are genetically MRSA but phenotypically MSSA. The double locus assay also yielded 36 Sa442-positive mecA-negative results, one was MRSA (false negative) and 35 were MSSA (true negative). The double locus assay also yielded 16 Sa442-negative mecA-positive results, and all 16 were MR-CoNS (true negative for MRSA). The double locus assay also yielded 22 Sa442-negative mecA-negative results, 9 of which were MSSA (true negative), 8 of which were MSCoNS (true negative) and 5 were non-*Staphylococcus* (true negative). The double locus assay resulted in a specificity of only 61.4% and a positive predictive value of 82.6% in detecting a mixed culture sample.

Example 3

Demonstration of Superior Accuracy of Triple Locus and Cycle Threshold Assays A triple locus high density multiplex qRT-PCR assay mixture was developed containing 17 oligonucleotides (SEQ ID NOs: 1-17). This multiplex assay mixture was tested on the same 460 patient DNA samples derived from swabs. The reactions were run using the standard qRT-PCR protocol described above with amplification and detection performed using a RotorGene 3000 System Real Time PCR instrument from Corbett Life Science.

The method of the present invention provides a two step process for analyzing results to substantively reduce false negative and false positive results. The first step is to separate results according to four classifications:
1. Positive on all 3 loci=MRSA
2. Negative on Sa442=Not MRSA
3. Positive on Sa442 and negative on mecA=Not MRSA
4. Positive on Sa442, positive on mecA and negative on SCC;orfX=Go to Step Two Based on the first step analysis, 203 samples met the criteria of the first classification. 202 were correctly identified as MRSA and one sample was positive on all 3 loci and yet found to be a false positive, reflecting in fact a mixture of two species, an MSSA (SCC:orfX-positive Sa442-positive mecA-negative) and a MR-CoNS (mecA-positive).

38 samples met the criteria for the second classification and all were correctly identified as not being MRSA. 36 samples met the criteria for classification 3. All were correctly identified as not being MRSA except for one that was found to be a false negative, probably a result of a MRSA strain with a mutated mecA gene at the site of the primers or probe, resulting in a negative mecA reaction.

61 samples met the criteria for the fourth classification and these were subjected to the second step analysis prescribed by the invention, namely comparison of the cycle threshold for the Sa442 and the cycle threshold for the mecA. In 18 cases, the cycle thresholds (CT: the cycle at which samples are first detected—reflecting the concentration of the targeted gene) for the two assays were within three CT values of one another, suggesting that the positive signal of mecA gene and Sa442 gene were coming from the same organism, or if it is a mixture, both organisms are at the same concentration. Of these 18, 16 were MRSA and 2 were MSSA, however all these were declared MRSA. In 43 cases, the cycle times for the two assays were more than three CTs, suggesting that these samples did not contain MRSA and instead that the positive mecA detection reflected one specie and the positive Sa442 detection reflected a different specie. As predicted, all 43 of these samples proved to contain mixtures reflecting MSSA and a MR-CoNS.

The combined assay resulted in a sensitivity of 99.6%, a specificity of 97.4%, a positive predictive value of 98.6% and a negative predictive value of 99.1% in detecting MRSA from mixed culture samples, thus demonstrating the increased accuracy and specificity of the assays of the present invention over both the double and single locus assays traditionally used to detect antibiotic-resistant bacteria such as MRSA.

Example 4

Triple Locus Assay Using Ambient Temperature-Stabilized qRT-PCR Mixture

An ambient temperature qRT-PCR reaction mix was developed containing buffer x1 (10 mM Tris pH 8.3, 50 mM KCl), $MgCl_2$, dNTPs mix, 1.5 units to 2.5 units of Hot Start Thermophilic DNA polymerase and stabilizing agents. 25 microliters of mix were placed into PCR microtubes, and the hydration was reduced in each microtube by at least 50%. The microtubes were subsequently stored at ambient temperature.

The triple locus high density multiplex qRT-PCR assay, containing 17 oligonucleotides (as described in Example 3, herein above) was added to microtubes containing the ambient temperature qRT-PCR reaction mix. The multiplex assay mixture was tested on 20 known patient DNA samples plated from swabs and four control samples. The reactions were run using the standard qRT-PCR protocol described above with amplification and detection performed using a RotorGene 3000 System Real Time PCR instrument from Corbett Life Science.

The results of this assay are presented in Table 4. All 24 assays performed exactly as predicted, detecting the precise gene targets of interest. Following the two step protocol of the invention for analysis of results as described in Example 3 above, it was possible to differentiate between samples containing MRSA and samples not containing MRSA with 100% accuracy. The results demonstrate the utility for identification of MRSA and discrimination of MRSA from non-MRSA bacteria from clinical patient samples of an ambient stabilized kit using assays of the present invention.

TABLE 4

| Type | Scc: orfX | Sa442 | Control | mecA |
| --- | --- | --- | --- | --- |
| 8 MRSA | + | + | + or − | + |
| 4 MSSA | − | + | + or − | − |
| 4 MR-CoNS | − | − | + or − | + |
| 1 orfX neg. MRSA | − | + | + or − | + |
| 2 MS-CoNS | − | − | + | − |
| 2 PL | − | − | + | − |
| 2 Template Control | − | − | − | − |

Example 5

Discrimination of MRSA from MSSA, MS-CoNS and MR-CoNS

A total of 29 experimental samples containing a mixture of known *Staphylococci* DNA were prepared. None of these samples contained *Staphylococci* DNA that included SCC:orfX genetic markers that could be detected using the single locus assay for detection of MREJ types i, ii, iii, iv or v. SCC:orfX is also referred to herein as the "bridging region".

Samples 1-4 each contained Methicillin Sensitive *Staphylococcus aureus* (MSSA) found positive for the Sa442 gene and negative for the mecA polynucleotide, in one of four different logarithmic concentrations.

Samples 2-8 each contained Methicillin Resistant Coagulase-negative *Staphylococci* (MR-CoNS) found positive for the mecA polynucleotide and negative for the Sa442 polynucleotide, in one of four different logarithmic concentrations.

Samples 9-13 contained a mixture of known *Staphylococci* DNA, reflecting a fixed concentration of MSSA plus one of five different logarithmic concentration levels of MR-CoNS.

Samples 14-18 contained a mixture of known *Staphylococci* DNA, reflecting a fixed concentration of MR-CoNS plus one of five different logarithmic concentration levels of MSSA.

Samples 19-22 contained known MRSA found positive for the Sa442 polynucleotide and positive for the mecA polynucleotide in each of four different Log concentration levels.

Samples 23-26 duplicated samples 19-22, reflecting known MRSA found positive for the Sa442 gene and positive for the mecA gene in each of four different Log concentration levels.

Samples 27-29 reflected three additional known MRSA isolates found positive for the Sa442 polynucleotide and positive for the mecA polynucleotide all at an optimal working concentration.

Seven additional samples were prepared as controls.

Samples 30-31 reflected two different concentration levels of known MRSA DNA, found positive for all three genetic loci: the Sa442 polynucleotide, the mecA polynucleotide and SCC:orfX.

Samples 32-33 duplicated samples 30 and 31.

Sample 34 contained known DNA from an MR-CoNS found positive for the mecA gene and negative for the Sa442 polynucleotide.

Sample 35 contained a sample of known MRSA DNA found positive for the Sa442 gene, positive for the mecA gene and negative for SCC:orfX.

Sample 36 contained no DNA.

qRT-PCR amplification and detection was performed on the experimental and control samples using the triple locus high density assay of the invention, using the standard qRT-PCR reaction mixture, reaction protocol and instrument described previously.

All of the experimental and control samples performed exactly as expected, demonstrating positive or negative findings as the case would be for SCC:orfX, the Sa442 polynucleotide and the mecA polynucleotide.

Twenty-one of the samples (items 9-29 and 35) were designed to reflect the positive finding of an S. aureus-specific polynucleotide (such as Sa442), the positive finding of the mecA polynucleotide, but negative for evidence of the SCC:orfX genetic region, originated from SCC:orfX negative MRSA (items 19-29 and 35) or mixtures of MSSA and MR-CoNS at different concentrations (items 9-18). The protocol of the invention provides a second step analysis process for samples that are found to be positive for an S. aureus-specific polynucleotide (such as Sa442) and positive for the mecA gene, but negative for SCC:orfX, namely to compare the cycle threshold of the S. aureus specific marker detection against the cycle time of the mecA detection in order to determine if the sample contains MRSA or reflects a mixture of two non-MRSA species.

The second protocol step analysis process was performed on the 21 experimental samples requiring the second step analysis. Detection of the Sa442 gene and detection of the mecA gene were found to have occurred within 3 CTs of each other for all samples containing MRSA. Accordingly, using the protocol of the invention, 100% of the experimental samples containing MRSA were correctly identified. Detection of the Sa442 gene and detection of the mecA gene were found to have accrued at an interval of 4 CTs or greater for all mixed experimental samples containing MSSA and MR-CoNS, and not containing MRSA except the 2 samples (item 12 and 15) which contained identical concentration of MSSA and MR-CoNS.

In summation, the protocol of the invention was found to be 100% accurate in discriminating mixed samples containing MSSA and MR-CoNS from samples containing MRSA with an atypical variant SCC:orfX region not detectable using the single locus assay of Huletsky et al.

The results from this assay for distinguishing between different species are illustrated in FIGS. 2 and 3. As shown in FIG. 2, MRSA and MSSA bacteria were distinguished from one another based on detection of the products of amplification reactions directed to the bridging region (also referred to herein as SCC:orfX), the mecA gene region, an S. aureus-specific polynucleotide sequence (in this embodiment, the nuc gene), and a human beta globin polynucleotide sequence (used as an internal control). In the MRSA samples, all four amplification products were detected. In contrast, in the MSSA samples, only the S. aureus-specific and the internal control human beta globin polynucleotide were detected.

Similarly, FIG. 3 shows the results of assays in which amplification reactions were directed to the bridging region, the mecA gene region, an S. aureus-specific polynucleotide sequence (in this embodiment, the nuc gene), and a human beta globin polynucleotide sequence (used as an internal control). In this case, for the samples containing MR-CoNS, the mecA gene polynucleotide sequence and the internal control polynucleotide sequences were detected, whereas in samples containing MS-CoNS, only the internal control polynucleotide sequence was detected. Thus, the assays of the present invention provide the ability to distinguish among MRSA, MSSA, MR-CoNS and MS-CoNS bacteria.

Example 6

Shelf Life Stability of a QRT-PCR Reaction Mixture and Multiplex Assay

An experiment was performed to establish the performance and shelf life stability of a multiplex assay QRT-PCR mix incorporating oligonucleotide primers and dual fluorescent labeled oligonucleotide probes.

An ambient temperature qRT-PCR Mix was prepared as described above in Example 4.

One primer-probe set targeting human β-Hemoglobin was prepared and purified consisting of forward and reverse primers (SEQ ID NOs: 21 and 22) and a probe of with a HEX fluorescent label added to the 5'-end and BHQ1 quencher label added to the 3'-end (SEQ ID NO: 23). A second primer-probe set targeting the human RNase-P gene was purchases from Applied Biosystems Inc. (TaqMan® RNase P Detection Reagents Kit, Part Number 4316831), consisting of a forward primer, a reverse primer and a TaqMan® Probe labeled with FAM at the 5'-end and TAMRA at the 3'-end.

All four primers and two probes were added to the ambient temperature qRT-PCR Mix prior to the hydration reduction process. These primers and probes were also added to a second microtube containing all of the components of the ambient temperature qRT-PCR Mix but stored at −20° C. to serve as a control.

After five weeks, a tube stored at room temperature containing the dehydrated PCR mix and duplex primer-probe assay was rehydrated and a second tube containing the control mix was removed from the freezer and defrosted. 100 ng of human DNA was added to each tube and the mixtures were amplified in a RotorGene 6000 System Real Time PCR instrument from Corbett Life Science according to the following protocol: First, fifteen minute hold cycle at 95° C. This was followed by fifty cycles each with three steps. Step one was at 95° C. for fifteen seconds, step two was at 55° C. for twenty seconds and step three was at 72° C. for thirty seconds.

The first round of experimentation was performed immediately following the PCR reactions and was as follows: The primer-probe assay targeting human β-Hemoglobin yielded the following results. The sample that was stored at −20° C. yielded a CT value of 23.30 and the sample stored at room temperature yielded a CT value of 23.46. The primer-probe assay targeting human RNase-P yielded the following results.

The sample that was stored at −20° C. yielded a CT value of 25.79 and the sample stored at room temperature yielded a CT value of 26.08.

The second round of experimentation was conducted five weeks later. The procedure was identical to that described above, with the exception that two tubes stored at room temperature and one tube stored at −20° C. were utilized in the experiment. To each of the three tubes 100 ng of human DNA was added and each was then amplified as described above.

The results of the second round of experimentation were as follows. The primer-probe assay targeting human β-Hemoglobin yielded the following results: the sample that was stored at −20° C. yielded a CT value of 25.42 and the two samples stored at room temperature yielded a CT value of 25.46 and 26.06. The primer-probe assay targeting human RNase-P yielded the following results: The sample that was stored at −20° C. yielded a CT value of 23.09 and the two samples stored at room temperature yielded a CT value of 23.50 and 23.65.

After ten weeks, the difference in effectiveness between the stabilized mixtures of the invention left sitting out at room temperature and comparable mixtures stored at −20° C. was less than one cycle. These results are illustrated in FIG. 4. The results clearly demonstrate the utility and stability at room temperature of the PCR mixes for multiplex Real-Time PCR.

Example 7

High Density Triple Locus qRT-PCR Assay and Comparison of Cycle Thresholds Across the Triple Locus for Detecting MRSA in Single and Mixed Bacterial Samples and Differentiating MRSA from MSSA, MR-CoNS and a Mixed Sample of MSSA & MR-CoNS A triple locus multiplex qRT-PCR assay mixture was developed containing four sets of primers and probes, for a total of 12 oligonucleotides (SEQ ID NOS: 1-2, 9-11, 15-17, 18-20 and 24). One pair of amplification primers and a dual labeled probe were designed to amplify and detect the mecA gene (SEQ ID NOs: 9-11). A second pair of primers and a dual labeled probe were designed to amplify and detect the *S. aureus*-specific nuc gene (SEQ ID NOs: 18-20). A third set of primers and a dual labeled probe were designed to amplify and detect the region of the orfX gene surrounding the insertion site for the SCCmec element in *S. aureus* bacteria as would amplify in an MSSA that does not contain the SCCmec element (SEQ ID Nos: 1-2 and 24). A fourth set of primers and a dual labeled probe designed to amplify and detect human β-globin to serve as a control assay (SEQ ID NOs: 15-17).

An ambient temperature qRT-PCR reaction mix was developed containing the triple locus multiplex qRT-PCR assay of the invention, plus buffer x1 (10 mM Tris pH 8.3, 50 mM KCl), $MgCl_2$, dNTPs mix, 1.5 units to 2.5 units of Hot Start Thermophilic DNA polymerase and stabilizing agents. 25 microliters of mix were placed into PCR microtubes, and the hydration was reduced in each microtube by at least 50%. The microtubes were subsequently stored at ambient temperature.

This ambient temperature multiplex assay mixture was tested with DNA samples of known, MRSA, MSSA, MS-CoNS and MR-CoNS strains. The assay was tested on two samples of each of the following DNA samples:
1. Pure MRSA
2. Pure MSSA
3. Pure MR-CoNS
4. A mixed sample of β-globin and MS-CoNS as a control
5. A mixed sample of MSSA and MS-CoNS
6. A mixed sample of MRSA and MSSA in equal concentrations
7. A mixed sample of MRSA, MSSA & MR-CoNS in equal concentration
8. A mixed sample of MRSA and MSSA in 1:10 ratio concentrations
9. A mixed sample of MRSA and MSSA in 10:1 ratio concentrations
10. A mixed sample of MSSA and MR-CoNS in equal concentrations
11. A mixed sample of MSSA and MR-CoNS in 1:10 ratio concentrations
12. A mixed sample of MSSA and MR-CoNS in 10:1 ratio concentrations The reactions were run using the standard qRT-PCR protocol described above with amplification and detection performed using a RotorGene 3000 System Real Time PCR instrument from Corbett Life Science.

The method of the present invention provides a two step process for analyzing results to substantively reduce false negative and false positive results. The first step is to separate results according to five classifications (1=mecA, 2=nuc, 3=MSSA-orfX, as provided in Table 2):
1. Positive on 1+2 and negative on 3=MRSA and not MSSA
2. Positive on 2+3 and negative on 1=MSSA and not MRSA
3. Positive on 1 and negative on 2+3=MR-non-*S. aureus* bacteria and neither MRSA nor MSSA.
4. Negative on all three and positive on the control=not MRSA, MSSA nor MR-non-*S. aureus* bacteria
5. Positive on 1+2+3=Go to Analysis Step Two and compare the CT values of the different amplicons.

Based on the first step analysis, the assay performed as predicted with all 24 samples, detecting the precise gene targets of interest. As expected, all three of the loci were detected in all of the samples containing MSSA plus one or more methicillin resistant bacteria, and these were subjected to the second step analysis prescribed by the invention, namely comparison of the cycle thresholds (CT: the cycle which are considered to be positive—reflecting the concentration of the targeted gene) for each of the three targeted genes.

As predicted, the cycle thresholds of the nuc assay and MSSA-orfX were within three CTs of each other for all of the mixed samples containing MSSA and not containing MRSA, suggesting that the positive signal of nuc gene was coming from the same MSSA organism as the MSSA-orfX region and not from a separate MRSA organism. Similarly, the cycle thresholds of the nuc assay and the MSSA-orfX were four CTs or greater of each other for all of the mixed samples containing MSSA and MRSA in non-equal concentrations (samples: 8, 9), suggesting that the positive signal of nuc gene was coming from a combination of the MSSA organism producing the positive MSSA-orfX signal and an MRSA organism.

Following the two-step protocol of the invention for analysis of results, it was possible to differentiate between the samples containing MRSA and samples not containing MRSA in non-equal concentrations (samples 8, 9) with 100% accuracy. The results demonstrate the utility for identification of MRSA and discrimination of MRSA from non-MRSA bacteria of the triple-locus assay and protocol of the present invention in both pure and mixed samples of unequal concentrations.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A kit that comprises:
   (a) a first set of primers complementary to at least a portion of a mecA polynucleotide sequence;
   (b) a second set of primers complementary to at least a portion of a bridging region;
   (c) a third set of primers complementary to at least a portion of an MSSA-orfX polynucleotide sequence: and
   (d) at least one member selected from: a DNA polymerase enzyme, (dNTPs, magnesium and a stabilizer.

2. A method of identifying bacteria in a sample, said method comprising:
   (a) providing a kit according to claim 1;
   (b) determining whether a mecA polynucleotide is present in said sample using said first set of primers;
   (c) determining whether a bridging region sequence is present in said sample using said second set of primers; and
   (d) determining whether an MSSA-orfX polynucleotide is present in said sample using said third set of primers, wherein the combination of (b), (c) and (d) present in said sample identifies bacteria in said sample.

3. A kit for detecting an antibiotic-resistant bacterial strain in a sample, wherein said kit comprises:
   (a) a first set of primers, wherein said first set of primers are capable of producing a first amplification product from at least a portion of a gene, wherein said gene confers antibiotic-resistance;
   (b) a second set of primers, wherein said second set of primers are capable of producing a second amplification product from at least a portion of a bridging region;
   (c) a third set of primers, wherein said third set of primers are capable of producing a third amplification product from at least a portion of a bacterial strain-specific polynucleotide sequence.

* * * * *